United States Patent [19]

Laske et al.

[11] Patent Number: 5,720,720

[45] Date of Patent: Feb. 24, 1998

[54] CONVECTION-ENHANCED DRUG DELIVERY

[75] Inventors: Douglas W. Laske, Rockville, Md.; Edward H. Oldfield, Philomont, Va.; Richard Hunt Bobo, Jackson, Mass.; Robert L. Dedrick, McLean, Va.; Paul F. Morrison, Bethesda, Md.

[73] Assignee: The United States of America as represented by the Department of Health and Human Services, Washington, D.C.

[21] Appl. No.: 616,785

[22] Filed: Mar. 15, 1996

Related U.S. Application Data

[63] Continuation of Ser. No. 112,370, Aug. 27, 1993, abandoned.

[51] Int. Cl.$^6$ ............................................. A61M 31/00
[52] U.S. Cl. ............................................. 604/49; 604/21
[58] Field of Search ............................. 604/19–22, 53, 604/49, 65, 67, 30, 118, 140, 141, 143, 146, 147, 149, 151, 156, 169, 207, 236, 247, 891.1

[56] References Cited

U.S. PATENT DOCUMENTS

| | | | |
|---|---|---|---|
| 3,690,318 | 9/1972 | Gorsuch | 128/DIG. 12 X |
| 4,403,985 | 9/1983 | Boretos | 604/53 |
| 4,447,224 | 5/1984 | Derant, Jr. et al. | 604/67 |
| 4,573,968 | 3/1986 | Parker | 604/67 |
| 4,648,869 | 3/1987 | Bobo, Jr. | 604/49 |
| 4,714,460 | 12/1987 | Calderon | 604/28 |
| 4,796,637 | 1/1989 | Mascuch et al. | 128/658 |
| 4,801,297 | 1/1989 | Mueller | 604/280 |
| 4,871,351 | 10/1989 | Feingold | 604/66 |
| 4,883,459 | 11/1989 | Calderon | 604/28 |
| 4,919,649 | 4/1990 | Timothy et al. | 604/65 |
| 4,931,050 | 6/1990 | Idriss | 604/891.1 |
| 4,973,319 | 11/1990 | Melsky | 604/247 |

(List continued on next page.)

FOREIGN PATENT DOCUMENTS

| | | |
|---|---|---|
| 0 537 136 A2 | 10/1987 | European Pat. Off. . |
| 0 364 799 | 9/1989 | European Pat. Off. . |
| 0 476 796 A1 | 9/1991 | European Pat. Off. . |
| 1417013 | 12/1972 | United Kingdom . |
| 9310830 | 11/1992 | WIPO ............................ 604/151 |

OTHER PUBLICATIONS

Lamb, S., *Interstitial Radiation for Treatment of Primary Brain Tumors Using the Brown–Roberts–Wells Stereotaxic System*, J. Neurosurgical Nursing, vol. 17, pp. 22–29 (1985).

*Primary Examiner*—Michael Powell Buiz
*Assistant Examiner*—At Nguyen
*Attorney, Agent, or Firm*—Lowe Price LeBlanc & Becker

[57] ABSTRACT

A method of high-flow microinfusion which provides convection-enhanced delivery of agents into the brain and other solid tissue structures. The method involves positioning the tip of an infusion catheter within a tissue structure and supplying an agent through the catheter while maintaining a pressure gradient from the tip of the catheter during infusion. Agent delivery rates of 0.5 to 15.0 μl/min have been used experimentally with infusion distances greater than 1 cm from the delivery source. The method can be used to delivery various drugs, protein toxins, antibodies for treatment or imaging, proteins in enzyme replacement therapy, growth factors in the treatment of various neurodegenerative disorders and viruses and gene therapy. An infusion catheter developed for the high-flow microinfusion includes a plurality of elongated slits adjacent a tapered portion of the catheter which are parallel to the axis of the catheter and spaced symmetrically about the circumference thereof. The infusion catheter is used in a convention-enhanced delivery system in which, after the infusion catheter is positioned in a tissue situs, it is connected to a pump which delivers a desired agent and maintains a desired pressure gradient throughout delivery of the agent.

13 Claims, 12 Drawing Sheets

U.S. PATENT DOCUMENTS

| | | | |
|---|---|---|---|
| 4,988,337 | 1/1991 | Ito | 604/154 |
| 5,066,490 | 11/1991 | Neville, Jr. et al. | 424/85.91 |
| 5,147,334 | 9/1992 | Moss . | |
| 5,181,910 | 1/1993 | Scanlon | 604/67 |
| 5,195,524 | 3/1993 | Takiguchi et al. | 128/653.3 |
| 5,208,021 | 5/1993 | Johnson et al. | 424/85.91 |
| 5,209,717 | 5/1993 | Schmoll et al. | 604/5 |
| 5,267,960 | 12/1993 | Hayman et al. | 604/106 |
| 5,300,048 | 4/1994 | Drewes, Jr. et al. | 604/280 |
| 5,538,726 | 7/1996 | Order | 424/178.1 |

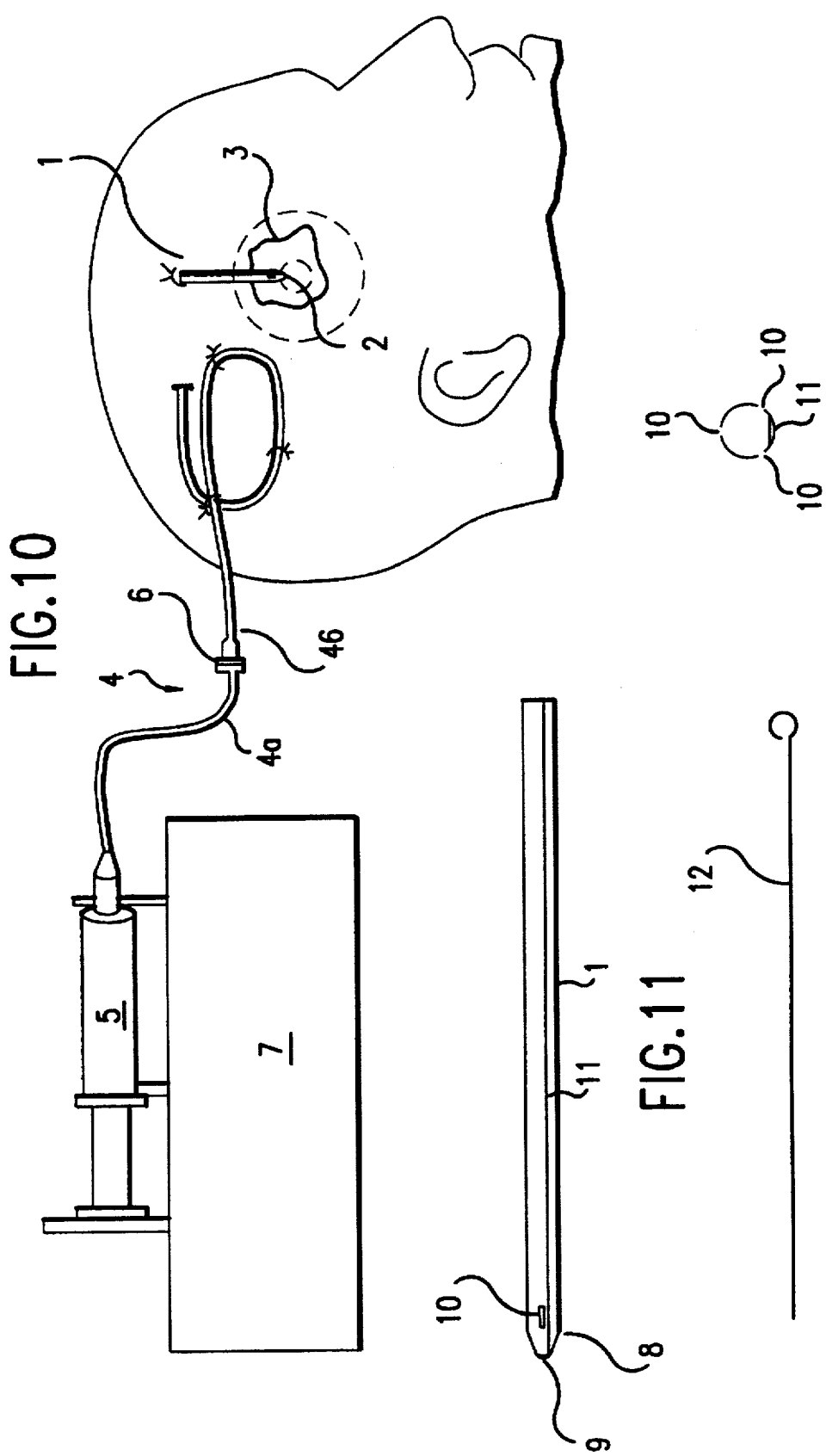

CONVECTION-ENHANCED DRUG DELIVERY

This is a continuation of application Ser. No. 08/112,370 filed Aug. 27, 1993, now abandoned.

TECHNICAL FIELD

The present invention relates to drug delivery systems and methods for delivering drugs into the brain of a subject, tumors and similar tissue structures. More particularly, the present invention is directed to drug delivery systems and methods which utilize convection-enhanced delivery.

BACKGROUND ART

Limited penetration into the central nervous system after systemic administration of most drugs has been known since Ehrlich first described the blood-brain barrier (BBB) in 1885. This limitation is most pronounced with high molecular weight and polar molecules. Many new drugs with therapeutic potential are polar proteins with a high molecular weight (growth factors, enzymes, antibodies, protein conjugates, genetic vectors). One strategy to circumvent the BBB and to improve drug delivery to the CNS is direct administration into the CSF or the brain parenchyma. However, ventriculocisternal perfusion relies on diffusion for distribution into the brain parenchyma and poor penetration occurs, even with drugs with ideal characteristics for diffusion. Penetration from CSF into the brain is extremely limited for high molecular weight compounds. After direct administration into the brain, limited diffusion in the brain severally retards the rate of distribution of such compounds.

Intratumoral chemotherapy for brain tumors has been administered by direct injection, intracavitary instillation, intracavitary topical application, chronic low-flow microinfusion, and controlled release from polymer implants. Intracavitary delivery has also been used to deliver biological reagents, including interferons and interleukin-2, to tumor. However, the efficacy of intratumoral drug administration is restricted by the poor diffusion of drug through tumor and brain interstitium relative to tissue clearance so that only a small volume of tissue surrounding the drug source is treated. Thus, poor drug delivery to the CNS limits application of promising basic findings for further research and treatment of neurological diseases such as neurodegenerative disorders, central nervous system tumors and inborn errors of metabolism.

Diffusion of a compound in a tissue depends solely on the free concentration gradient and the diffusivity of that compound in that tissue. It is very slow for high molecular weight compounds in tumor and normal tissues. Diffusion of IgG in tumor requires 3 days to reach 1 mm from the point of origin. Low molecular weight compounds, on the other hand, have a higher diffusivity in brain and tumor, but loss via capillaries and (for some) metabolism generally limit therapeutic drug levels to a few millimeters from the source of drug.

Fluid convection, or bulk flow, in tissues occurs as a result of pressure gradients. Bulk flow of brain interstitial fluid occurs under normal conditions, with vasogenic edema, and after infusion of solutions directly into the brain parenchyma. Furthermore, bulk flow of brain interstitial fluid alters the distribution of Dextran Blue dye ($2 \times 10^6$ MW) injected intracerebrally. The present invention is directed to fluid convection within the brain which is established by maintaining a pressure gradient during interstitial infusion. This method can be used to supplement diffusion and greatly enhance the distribution of small and large molecules, including high molecular weight proteins.

The need for improved delivery of high molecular weight compounds to the brain is an issue that presents itself in newly developing approaches to cancer therapy, the treatment of Parkinson's disease, enzyme replacement therapy, and gene therapy. The principal requirement is to deliver these substances to the interstitial space regionally, but over volumes that are on the scale of gross brain structures. For example, in the case of tumor therapy, one may wish to expose much of the white matter in one hemisphere to antibody-conjugates in an attempt to destroy widely dispersed metastatic cells or fragments of tumor that project well beyond the main tumor mass. Intravenous or intraarterial administration of macromolecules is capable of delivery to the brain interstitial space, but only at very low concentrations or over very long dosage periods due to the low capillary permeability of brain tissue. Furthermore, especially for tightly-bound macromolecules, effective intercapillary diffusion times may be extremely long, and it is possible that cells lying midway between capillaries may escape exposure.

Methods that involve administration of the agent directly into the interstitial space circumvent these problems, but since these methods require finite non-distributed sources, they also introduce new questions about the extent of penetration into the tissue surrounding the source. These methods include low-flow microinfusion (direct interstitial infusion) and release of bioactive agents from polymeric implants. In both methods, delivery to surrounding tissue depends on diffusion from the source as well as loss due to permeation and reaction. The balance between these source and sink rates determines the penetration depth. Such balances may lead to steady state radial penetration distances of only a few millimeters when distances on the centimeter scale are needed.

The present invention provides fluid convection into the brain and tumor structures which is established by maintaining a pressure gradient during interstitial infusion which can be used to supplement diffusion and enhance distribution of small and large molecules, including high molecular weight proteins, to a much larger volume of the brain tissue than is achievable by diffusion alone.

DISCLOSURE OF THE INVENTION

It is accordingly one object of the present invention to provide a method for delivering drugs into and through various tissue structures.

Another object of the present invention is to provide a method for delivering drugs into and through various tissue structures which utilizes convection-enhanced delivery.

It is a further object of the present invention to provide a method of high-flow microinfusion of drugs into tissue structures which involves inflow rates of up to about 15.0 µl/min.

A further object of the present invention is to provide an infusion catheter for high-flow microinfusion.

A still further object of the present invention is to provide a convection-enhanced drug delivery system.

According to these and further objects of the present invention which will become apparent as the description thereof proceeds, the present invention provides a method of administering an agent through a tissue structure by interstitial fusion which involves:

positioning a tip of the catheter within a tissue structure;

connecting the catheter to a source of an agent; and delivering an agent from the agent source to the catheter and out the catheter tip into the tissue structure while maintaining a pressure gradient at the catheter tip for at least 5 minutes.

The invention further provides an infusion catheter which includes a substantially cylindrical structure having a tapered tip at one end thereof and a plurality of elongated openings adjacent the tapered portion, the plurality of elongated openings each being parallel to a central axis of the infusion catheter and being symmetrically spaced along a circumference of the infusion catheter.

The present invention also provides a convection-enhanced agent delivery system which includes the infusion catheter in combination with a programmable pump and a connecting tube attached between the infusion catheter and the pump.

BRIEF DESCRIPTION OF THE DRAWINGS

The present invention will be described with reference to the attached drawings which are given by way of non-limiting examples only, in which:

in FIG. 4B.

in FIG. 5B.

FIG. 10 is a diagram of a convection-enhanced drug delivery system according to one embodiment of the present invention.

FIG. 11 is a side cross-sectional view of an infusion catheter according to one embodiment of the present invention.

FIG. 12 is axial cross-sectional view of the infusion catheter of FIG. 11.

FIG. 13 is a wire stylet for use in the infusion catheter of FIG. 11.

BEST MODE FOR CARRYING OUT THE INVENTION

Figure 1:
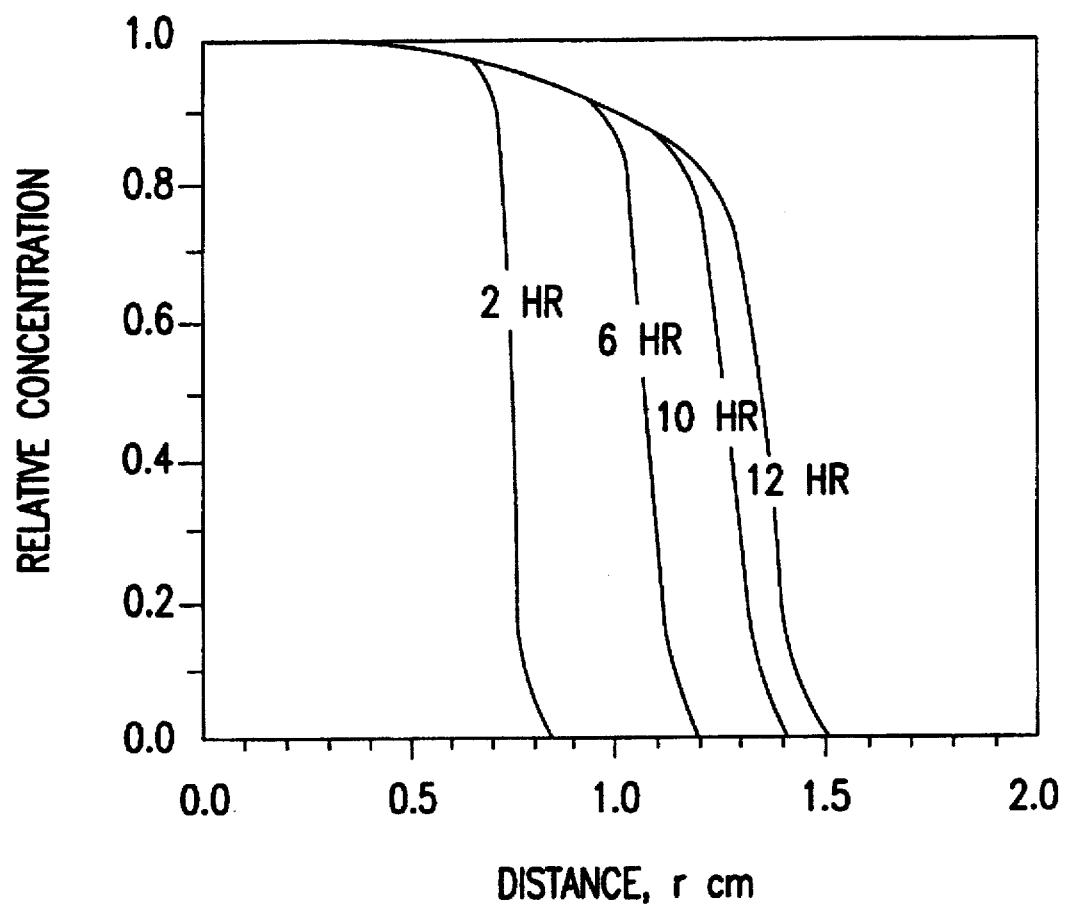
FIG. 1 shows the concentration profiles predicted at various times for a representative 180 kDa unbound macromolecule infused at 3 μl/min into a tissue with $\Phi=0.2$ and degraded at the rate of $K_{irr}=1.15\times 1^{-6}$ sec.$^{-1}$.

According to the present invention, penetration distances of various agents through brain, tumor and similar tissue structures are increased by the use of high-flow microinfusion (flow rates in the 0.5 to 15.0 μl/min range), rather than diffusive flow. During the course of the present invention the transport processes associated with the high-flow microinfusion of macromolecules has been studied and described and formulations for estimating the time-dependent penetration depths of these substances as well as the associated concentration profiles have been developed.

The infusion phase itself has been described by the present inventors primarily with regard to its dependence on bulk flow. In addition, the post-infusion phase has been described, where diffusional transport plays the major role. Corresponding expressions have also been developed for the alternative delivery technique of low-flow microinfusion. The concentration expressions for both low and high-flow microinfusion have been placed in two commonly-used descriptors of pharmacodynamics, area-under-the-curve (AUC) and threshold metrics, in order to predict the gain in penetration depth and treatment volume at fixed pharmacodynamic effect that the high-flow microinfusion of the present invention provides over low-flow diffusional delivery.

The transport analysis of the high-flow microinfusion phase developed during the course of the present invention builds upon the rigid pore transport model of Baxter and Jain (*Microvas. Res.* 37, 77–104 (1989)), but has been specialized to the brain and small catheter sources, using a Peclet analysis to obtain simplified results. The corresponding description of slow-flow delivery is an extension of the earlier microinfusion analysis of Morrison and Dedrick (*J. Pharm. Sci.* 37, 120–128 (1986)) and is similar to certain polymer implant formulations of Saltzman and Radomsky (*Chemical Engineering Science* 46, 2429–2444 (1991)) and the point source injection analysis of Nicholson (*Brain Res.* 333, 325–329 (1985)) and Nicolson and Rice (*Ann. New York Acad. Sci.* 481, 55–68 (1986)). The transport description of the post-infusional phase is developed from mass transfer concepts of Carslaw and Jaeger (*Conduction of Heat in Solids*, Oxford: Clarendon Press (1959)). Analytical mathematical methods have been employed whenever possible to clarify parameter dependence and to obtain end expressions that are relatively simple estimators of the concentration profiles that develop about the catheter tip.

The high-flow microinfusion theory developed during the course of the present invention was used to predict the magnitude of spread of a marker protein, transferrin, in the white matter of a cat as discussed in the example given below. Autoradiographic images of the protein within the corona radiata provided preliminary confirmation of agreement between observed spread of the macromolecule and prediction.

One goal of the present invention was to investigate the likely range of penetration depths, and associated pharmacodynamic effects, of molecules whose microvasculature permeabilities and metabolic constants may vary over a wide range. Based on our experimental transferrin infusion data, previous reports of edema associated with cold injury, and emplacement of microdialysis probes, the extracellular fraction due to deformation and injury was expected to lie between 0.4 and the normal value of 0.2, except for somewhat larger excursions within a millimeter of the catheter tip as one approaches the small fluid filled cavity that develops there. The present inventors have developed expressions for molecular transport which are based upon the same rigid medium assumptions employed by Baxter and Jain (*Microvas. Res.* 37, 77–104 (1989)), to which they have incorporated factors to account for the flux conditions required for infusion from a catheter, and limitations on the effects of deformation to be bounded by the results obtained for normal and edematous extracellular fractions.

The molecular transport model associated with infusion consists of two expressions, one describing the radial pressure distribution in tissue and the other the differential conservation of mass of infused substance.

Assumptions behind the model are: (1) the infused region of the brain is a homogeneous porous medium consisting of cells surrounded by a tortuous extracellular space through which all radial diffusive and bulk movements occur; (2) redial bulk movement is driven by the pressure gradient produced by the infusion pump in accordance with Darcy's law; (3) the brain region into which infusion takes place is sufficiently large so that the pressure gradient far from the catheter tip is effectively zero and the pressure at this distance is very near the CSF pressure; (4) water may be transported across microvascular membranes, uniformly distributed throughout the brain, in proportion to the difference between the interstitial pressure and the effective Starling pressure; (5) infused molecules may also leave the extracellular space in similar fashion, although subject to significant retardation at the membrane, or they may exit the space by simple pore diffusion; (6) the infused molecule is not significantly retarded by the interstitial matrix; (7) the volumetric rate of infusion is constant and sufficiently large at the catheter tip to equate the bulk flow in the tissue at the tip to the volumetric infusion rate; (8) infused species may bind linearly to immobile components in the extracellular space; (9) degradation of the infused species may occur by linear metabolism, either directly or subsequent to binding; (10) no lymphatics are present in brain and hence no loss may occur via this route; and (11) the infused substance is not produced endogenously.

In addition to the above assumptions, for purposes of the present invention both the extracellular fraction ($\phi$) and tissue hydraulic conductivity ($\kappa_i$) have been approximated as constant, although both actually depend on radius at high infusion rates. $\phi$ must decline from a deformed value near the catheter tip to the normal brain value at distant points, and $\kappa_i$, through its dependence on porosity and glycosoaminoglycan concentration, depends on radius through $\phi$. However, since the present invention is concerned with penetration distances, the extracellular fraction and tissue hydraulic conductivity can approximately be bound by selecting normal and edema-like values.

Given these assumptions, the expression for radial-dependent pressure can be derived from the equation of continuity for water and Darcy's law as:

$$p_i = p_e + \frac{q_v e^\alpha}{[4\pi\phi\kappa_i(1+\alpha)]} \frac{\exp[-(\alpha/\zeta)r]}{r} \quad (1)$$

where $p_i$ is the interstitial pressure, $p_e$ is the Starling pressure (Eq. A3), $q_v$ is the infusion volumetric flow rate, $\alpha^2 = L_p s \zeta^2 / (\phi\kappa_i)$, $L_p$ is the vascular hydraulic conductivity, s is the capillary surface area per unit volume of tissue, $\zeta$ is the catheter tip radius, and $\phi$ and $\kappa_i$ are as described above. For constant $\kappa_i$, this result indicates that pressure declines at least as rapidly as the inverse of the radius.

The remainder of the high-flow model is an expression describing the differential conservation of mass of infused macromolecular species. The general expression for the free interstitial concentration of the infused solute, $c_i$, consistent with linear binding and metabolism and the other assumptions above, is $$R_d \frac{\partial c_i}{\partial t} = D_e \nabla \cdot [\phi \nabla c_i] - \nabla \cdot [\phi v_i c_i] - \quad (2)$$

$$\{L_p s(1-\sigma)(p_e - p_i)/(e^{Pe_{mv}} - 1)\}c_i - \kappa_{irr} c_i$$

This expression indicates that, in a differential volume element of brain tissue, the time rate of change of the total concentration of infusate (left-hand-term, where $R_d c_i$ is the total free plus bound concentration) equals the net diffusion into that element (first right-hand-term) plus net gain due to bulk flow driven here by the infusion (second right-hand-term) less losses due to pore diffusion and bulk flow across microvasculature walls (third right-hand-term) less loss due to irreversible metabolism (fourth right-hand-term). $R_d$ accounts for the distribution between the intra- and extracellular spaces and linear binding. For a macromolecule that does not exchange with the intracellular space or enters the intracellular space only to undergo rapid irreversible degradation, $R_d = \phi(1 + k_{b1} B_o/k_{b2})$, where $B_o$ is the concentration of binding sites and $k_{b1}/k_{b2}$ is the affinity constant on an extracellular space basis. $D_e$ is the diffusion constant in the extracellular space, $\sigma$ is a reflection coefficient accounting for the retardation of infused species relative to water flow across the capillary endothelium, and $k_{irr}$ is a first order degradation constant on a total tissue basis. $Pe_{mv}$ is a microvasculature Peclet number which expresses the ratio of convection to diffusion across capillary walls. $Pe_{mv}$ is defined as $$Pe_{mv} = \frac{L_p s(p_e - p_i(r))(1-\sigma)}{ps} \quad (2a)$$

where p is the microvascular permeability of brain tissue. Boundary conditions associated with this differential mass balance are (1) zero concentration at distances far from the infusion catheter, and (2) a free interstitial concentration at the catheter tip ($r=\zeta$) equal to the infusate concentration of macromolecule, $c_o$.

For many macromolecular agents, further simplification of this model is possible. First, evaluation of the microvascular Peclet number, $Pe_{mv}$, for the typical macromolecular brain transport constants in Table 1 below indicates that diffusional permeation across capillary walls is dominant at distances beyond 0.074 cm.

TABLE 1

| Parameter | Symbol | Value | Source |
|---|---|---|---|
| Capillary hydraulic conductivity ($cm^3$/dyne/sec) | $L_p$ | $7.1 \times 10^{-13}$ | Paulson et al 1977(25) |
| Tissue hydraulic conductivity ($cm^4$/dyne/sec) | $\kappa_i$ | $1.7 \times 10^{-8}$ | This work[2] |
| Capillary permeability (cm/sec) | p | $1.1 \times 10^{-9}$ | Blasberg et al 1987(4) |
| Capillary area/tissue volume ($cm^2/cm^3$) | s | 100 | Bradbury 1979(5) |
| Reflection coefficient | $\sigma$ | 0.99 | Estimated[3] |
| Extracellular fraction | $\phi$ | 0.2–0.4 | Patlak et al 1975(24); Streicher et al 1964(321); Dykstra et al 1992(8) |
| Catheter radius (cm) | $\zeta$ | 0.032 | 23 gauge |
| Starting pressure (dyne/$cm^2$) | $P_\theta$ | 9996. | Marmarou et al 1980[4] |
| Diffusion coefficient ($cm^2$/sec) | $D_e$ | $1. \times 10^{-7}$ | Saltzman, Radomsky 1991[5] |
| Volumetric infusion rate ($cm^3$/sec) | $q_v$ | $5.0 \times 10^{-5}$ | Typical 3 μl/min high-flow infusion rate |
| Degradation rate constant ($sec^{-1}$) | $k_{irr}$ | 0. $1.15 \times 10^{-6}$ | no degradation Arbitrary |

[1]Typical of a 180 k Da protein.
[2]Interstitial conductivity for a rigid pore model to reproduce catheter tip pressure of 25 mm Hg observed experimentally upon initial establishment of free-flow into white matter at 1.15 μ/min.
[3]Value increased to 0.99 over the 0.95 peripheral tissue estimate of Covell et al (7) in order to account for greater reflection due to tight endothelial junctions in brain tissue.
[4]$p_\theta$ defined in Eq. A3. For brain, $p_\theta$ is very nearly the known cerebral spinal fluid pressures, reported by Marmarou et al (18) and confirmed in our laboratory as 7.5 mm Hg in the cat.
[5]Albumin $D_e$ value of these authors scaled by molecular weight to 180 kDa.
[6]This rate corresponds to a half-life of 33 hr and is roughly 5 times the average brain protein turnover rate (34).

The third right-hand term of Eq. 2 may therefore be replaced by its low $Pe_{mv}$ limit. (For deforming tissue that may maintain relatively high $P_i$ values for large distances, the $Pe_{mv}$ simplification would still hold provided the $(1-\sigma)/p$ ratio remains unchanged or is lowered). Second, a distant radial tissue Peclet number given by $$Pe_{tiss} = = \sqrt{q_v/(3D_e r)}$$

may also be evaluated using the parameters in Table 1. This bulk-to-diffusive flow ratio reaches 10 at 1.7 cm, indicating that macromolecules having diffusion constants less than $1 \times 10^{-7}$ $cm^2$/sec and infused at 3 μl/min have little radial diffusion out to at least this distance. Since this distance exceeds that likely to be accessed over the half-day infusions of primary concern to use, radial diffusion may be neglected relative to radial bulk flow, i.e., the first right-hand-term of Eq. 2 may be dropped. Hence for this special case, Eq. 2 reduces to $$R_d \frac{\partial c_i}{\partial t} = -\phi \nabla \cdot [v_i c_i] - K c_i \quad (3)$$

where $K = ps + k_{irr}$, $v_i$ is obtained from Darcy's law and the interstitial pressure (Eq. 1), $\phi$ is constant, and $\alpha$ is defined below Eq. 1. The simplest solution of this equation is $$c_i(r,t)/c_0 = \begin{cases} \exp\left[-\frac{4\pi K}{3q_v}(r^3 - \zeta^3)\right] & \zeta \leq r \leq [3q_v t/(4\pi R_d) + \zeta^3]^{1/3} \\ 0 & r > [3q_v t/(4\pi R_d) + \zeta^3]^{1/3} \end{cases} \quad (4)$$

where t is the experimental infusion time.

FIG. 1 shows the concentration profiles predicted at various times for a representative unbound macromolecule infused at 3 μl/min into a tissue with $\phi=0.2$ and degraded at the rate of $k_{irr}=1.15 \times 10^{-6}$ $sec^{-1}$. (Other parameters in Table 1.) These profiles were computed numerically from Eq. 2, and thus retain diffusive contributions. The typical shape of the profile is one that slowly declines, reflecting the cumulative transport of infused substance into the plasma and loss to reaction in each shell through which the infusate passes, then finally reaches a maximum penetration distance where the profile drops precipitously. The simple formula of Eq. 4 reproduces the slowly declining portion of this curve exactly and approximates the leading edge as a step. The slight curvature of the concentration front seen in FIG. 1 results from diffusion near the front; lower values of $D_e$ would reduce this curvature.

A characteristic penetration distance of a macromolecule may be estimated from Eq. 4 as the distance to the steady state profile inflection point, i.e., $$r_p = 3\sqrt{2q_v/(4\pi K)}.$$

The time of approach to this steady state distance can be calculated from rp and the inequalities of Eq. 4 as $t_p = 2R_d/(3K)$. For the macromolecules of FIG. 1, where $k_{irr}=1.15 \times 10^{-6}$ $sec^{-1}$ and $R_d=\phi=0.2$, $r_p$~1.8 cm and $t_p$~1.2 days. When no metabolism is present ($k_{irr}$_0), $r_p$ doubles but the time to approach steady state becomes very long, on the order of 14 days. However, even for the short infusion times of FIG. 1, the magnitude of penetration is on the same dimensional scale as many brain structures and thus indicates the potential for large scale dosing.

Concentration profiles are also described by the low microvascular Peclet ($Pe_{mv}$) limit of Eq. 2 except with the omission of the bulk flow (second right-hand) term. In addition, the inner boundary condition is replaced by one that requires the mass per unit time leaving the catheter to equal the diffusive flux through the tissue at the catheter tip. The expression for the low-flow interstitial concentration profile can be obtained by integration as $$c_i(r,t) = \frac{q_{vL} c_{oL}}{16 \pi a (D')^{3/2}} \left[ e^{2ab} erfc\left(\frac{a}{\sqrt{t}} + b\sqrt{t}\right) + e^{-2ab} erfc\left(\frac{a}{\sqrt{t}} - b\sqrt{t}\right) \right] \quad (5)$$

where r is the radial distance from the catheter tip, t is the infusion time, and $$a = r/(2\sqrt{D'}), b = \sqrt{K/R_d}, D' = \phi D_e/R_d$$

(This expression assumes a point source of material, i.e., $\zeta=0$.) $q_{vL} c_{oL}$ is the rate of mass inflow, where $q_{vL}$ is the low flow volumetric inflow rate and $C_{oL}$ is the associated infusate concentration. $q_{vL}$ must be chosen sufficiently low to avoid significant bulk flow near the catheter tip; from consideration of the radial Peclet number $Pe_{tiss}$, this condition can be satisfied if $q_{vL}=.05$ μl/hr or less. Furthermore, so that low- and high-flow infusion methods can eventually be compared on the same total dose basis, the total infusion times for both flow rates have been arbitrarily chosen to be equal and then constrained the total delivered mass of macromolecule to be the same in each case. Consequently, $q_{vL}c_{oL}=q_vc_o$, and since both flow rates have already been specified, the low-flow infusate concentration is to be $c_{oL}=(q_v/q_{vL})c_o=3600\ c_o$.

When considering the total effect of a drug on tissue following infusion, one must consider not only the pharmacodynamic effect during the infusion but also effects that continue to occur during the redistribution and clearance period that follows termination of infusion. Concentration profiles must therefore be calculated for this phase as well. In the case of a rigid pore model, infused solute molecules move solely by diffusion during this phase with the consequence that sharp profiles established at the end of infusion, such as those of FIG. 1, broaden and extend their range outward.

Such diffusionally broadened profiles may be computed by considering the concentration profiles that exist at the end of infusion (Eq. 4 for high-flow microinfusion, Eq. 5 for low-flow delivery) to represent a series of instantaneous shell sources, each of which may spread by diffusion during the post-infusion period. The complete post-infusion concentration profile may then be obtained by superimposing decaying time-dependent spherical shell solutions chosen to represent the appropriate $c_i(r,t)$ source. The final solution of this problem is $$c(r,t) = \frac{e^{-K't}}{2r(\pi D't)^{1/2}} \int_0^{r_{up}} c_i(r',t_{inf})r'[e^{-(r-r')^2/(4D't)} - e^{-(r+r')^2/(4D't)}]dr' \quad (6)$$

where D' is defined below Eq. 5, $K'=K/R_d$, $t=t-t_{inf}$, $t_{inf}$ is the appropriate infusion time for either high or low infusion (chosen here to be equal), and $$r_{up} = \{[3q_vt_{inf}/(4\pi R_d)]^{1/3} \quad \text{high flow microinfusion} \atop \quad\quad\quad\quad\quad\quad\quad\quad\quad\quad \text{low flow microinfusion}$$

For high-flow microinfusion, $c_i(r, t_{inf})$ is given by Eq. 4; for low-flow, by Eq. 5. Thus Eqs. 4 and 5 hold for all times up to $t_{inf}$, i.e., $t_{inf} > t > 0$, while Eq. 6 holds for all $t > t_{inf}$.

Figure 2A:
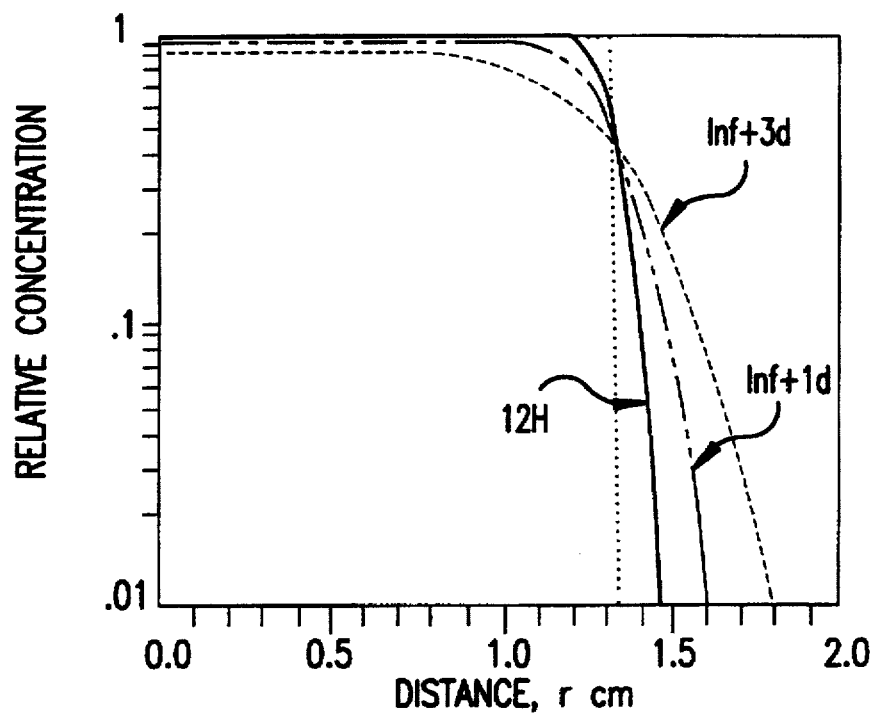
FIGS. 2A and 2B are interstitial concentration profiles of a macromolecule (CiCo) in non-binding brain tissue at the end of a high-flow microinfusion with zero metabolism (FIG. 2A) and with a metabolism characterized by a linear rate constant (FIG. 2B).
Figure 2B:
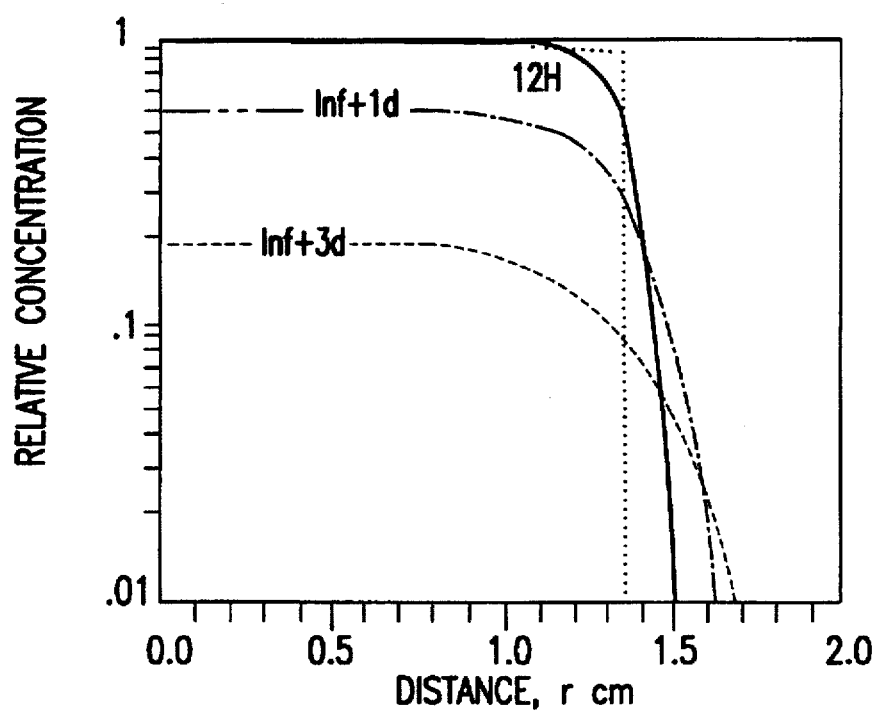

FIGS. 2A and 2B show the concentration profiles computed for non-binding macromolecules that are infused into brain tissue ($\phi=0.2$) at 3 μl/min for 12 hr ($t_{inf}=12$ hr) and then allowed to diffusionally relax for period of 1 and 3 days. FIG. 2A gives results when metabolism is absent, while FIG. 2B gives results when metabolism corresponds to a rate of macromolecular loss that halves molecular concentration in 33.5 hr (a rate about five-fold that of normal total brain protein turnover). The fine dotted line in FIGS. 2A and 2B indicates the location and shape of the concentration front when all radial tissue diffusion is ignored. Parameters other than metabolism are listed on Table 1. It is clear that diffusion may spread macromolecules well beyond the profile reached at the end of the infusion, and that these concentrations may persist for many multiples of the infusion time itself.

Figure 3A:
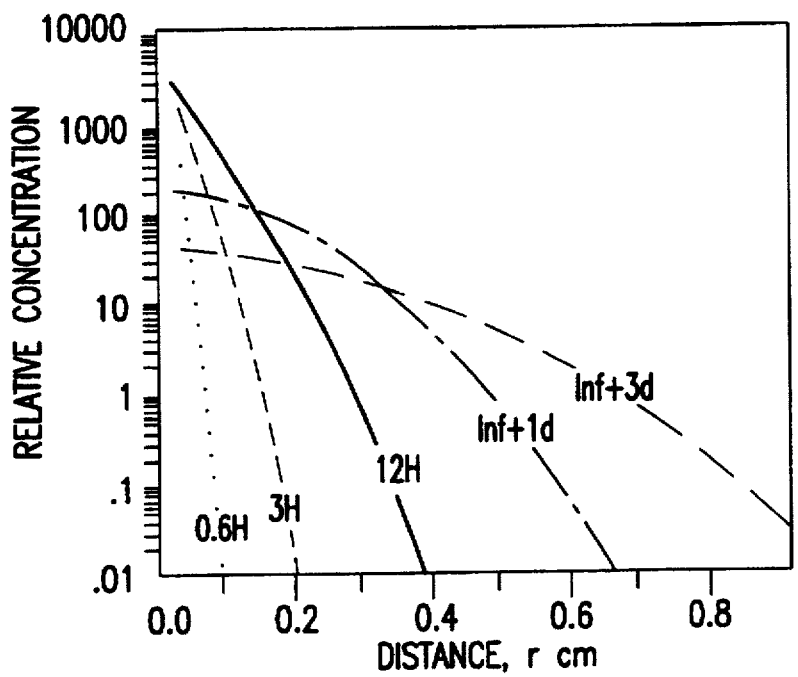
FIGS. 3A and 3B are interstitial concentration profiles of a macromolecule in non-binding brain tissue at the end of a low-flow microinfusion with zero metabolism (FIG. 3A) and with a metabolism characterized by a linear rate constant (FIG. 3B).
Figure 3B:
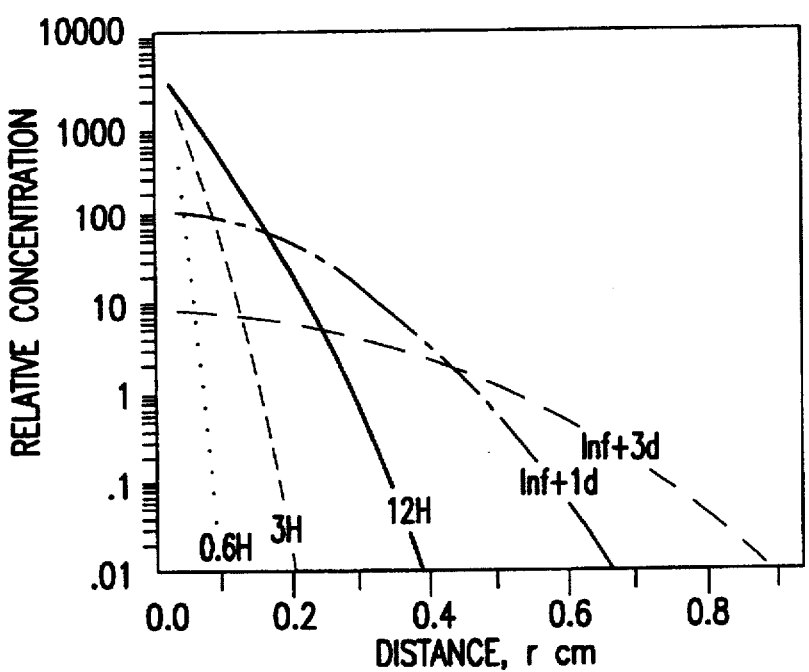

FIGS. 3A and 3B show the concentration profiles of a macromolecule (Ci/Co) in non-binding brain tissue at various times during a slow-flow (0.5 μl/hr) microinfusion of 12 hour duration, and at 1 day and 3 days after termination of infusion. Infusate concentration is 3600-fold larger than the high-flow infusate concentration in order to assure delivery of the same total mass of molecules. In FIG. 3A metabolism is zero. In FIG. 3B metabolism is characterized by a constant rate corresponding to a half-life of 33.5 hr. Other parameters are listed in Table 1.

Once again it can be seen that there is a persistent and substantial post-infusional spreading characterized by an absolute magnitude of diffusional spread comparable to that seen with the high-flow rate microinfusion results. The concentration range is much greater here because of the 3600 larger infusate concentration employed at low volumetric flow rate (to achieve the same delivered mass as at higher flow rate).

In order to contrast high-flow microinfusion with low-flow delivery, the radial dependence of expected pharmacodynamic effect has been computed for each method. Two pharmacodynamic metrics have been employed: (a) the time integral of the tissue concentration function, a given value correlating with a particular likelihood of end effect (the area-under-the-curve or AUC metric), and (b) the threshold concentration, significant pharmacodynamic interaction occurring only when tissue concentrations exceed this value (threshold metric).

$$AUC(r) = \int_0^{t_{inf}} c_i(r,t)dt + \int_0^{\infty} c(r,t)dt \quad (7)$$

where the first integral corresponds to the infusion period and the second to the post-infusional relaxation phase. $c(r,t)$ is given by Eq. 6. This formula applied to either delivery rate provided the corresponding $c_i(r, t_{inf})$ is appropriately taken from either Eq. 4 or 5. Because the denominator of the integrand in the second integral becomes zero at t=0 (due to the $t^{1/2}$ in the denominator of Eq. 6), it is convenient to carry out a partial integration to remove this complication.

The result of evaluating this integral for the bulk flow dominant situation (high volumetric flow) consists of two parts, depending on r and leads to $$AUC_{bulk}(r) = c_o \left[ t_{inf} - \frac{4\pi R_d}{3q_v}(r^3-\zeta^3) \right] \exp\left[ \frac{-4\pi K}{3q_v}(r^3-\zeta^3) + \right.$$

$$\frac{c_o}{2r\sqrt{K'D'}} \left\{ \int_0^x r'\exp\left[ \frac{-4\pi K}{3q_v}(r^3-\zeta^3) - \right. \right.$$

$$\sqrt{K'/D'}\ (r-r') \bigg]\ dr' +$$

$$\int_r^{[3q_vt_{inf}/(4\pi R_d)+\zeta^3]^{1/3}} r'\exp\left[ \frac{-4\pi K}{3q_v}(r^3 - \right.$$

$$\zeta^3) - \sqrt{K'/D'}\ (r-r') -$$

$$\int_0^{[3q_vt_{inf}/(4\pi R_d)+\zeta^3]^{1/3}} r'\exp\left[ \frac{-4\pi K}{3q_v}(r^3-\zeta^3) - \sqrt{K'/D'}\ (r+r') \right.$$

when $$r \leq [3q_vt_{inf}/(4\pi R_d) + \zeta^3]^{1/3} \quad \text{Case I}$$

and to $$AUC_{bulk}(r) = \quad (8b)$$

$$\frac{c_o}{2r\sqrt{K'D'}} \left\{ \int_0^{[3q_vt_{inf}/(4\pi R_d)+\zeta^3]^{1/3}} r'\exp\left[ \frac{-4\pi K}{3q_v}(r^3-\zeta^3) - \right. \right.$$

$$\sqrt{K'/D'}\left( r - \int_0^{[3q_vt_{inf}/(4\pi R_d)+\zeta^3]^{1/3}} r'\exp\left[ \frac{-4\pi k}{3q_v}r^3-\zeta^3 \right] \right) -$$

-continued $$\sqrt{K'/D'} \ (r+r')\ ] dr' \ \}$$

when $$r > [3q_v t_{inf}/(4\pi R_d) + \zeta^3]^{1/3} \quad \text{Case II}$$

The result for pure diffusional flow is $$AUC_{diff}(r) = \int_0^{t_{inf}} c_i(r,t)dt + \qquad (9)$$

$$\frac{1}{2r\sqrt{K'D'}} \ \{ \ \int_0^r r'c_i(r',t_{inf})\exp[-\sqrt{K'/D'} \ (r-r')]dr' +$$

$$\int_r^\infty r'c_i(r',t_{inf})\exp[-\sqrt{K'/D'} \ (r'-r)]dr' -$$

$$\int_0^\infty r'c_i(r',t_{inf})\exp[-\sqrt{K'/D'} \ (r+r')]dr' \ \}$$

where $c_i(r,t)$ is given by Eq. 5.

Figure 4A:
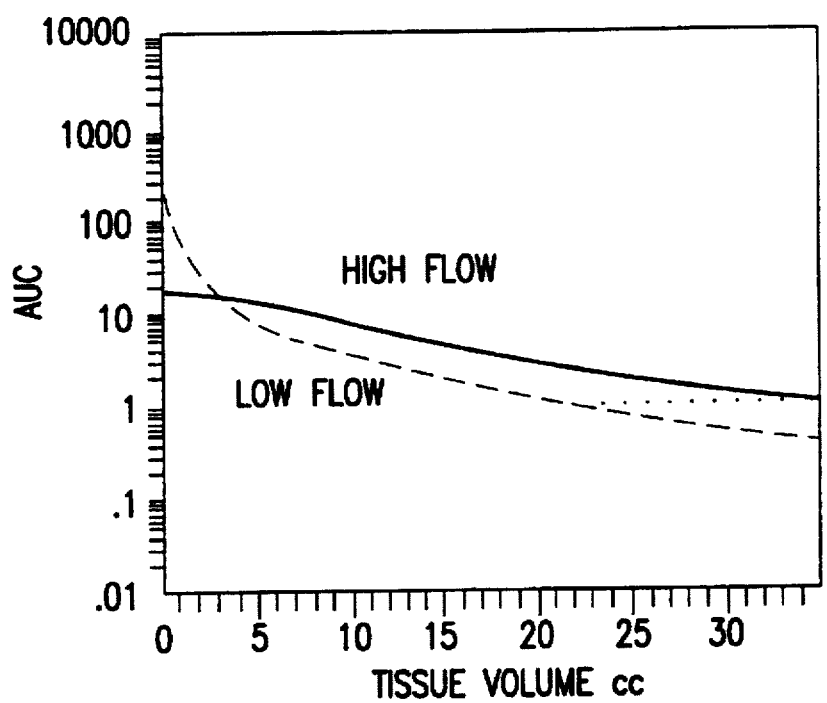
FIGS. 4A and 4B are area under the curve pharmacodynamic effects taken as a function of tissue volume corresponding to a radial position r. Ordinates are expressed in days since relative concentrations in this expression are non-dimensional. High-flow and low-flow lines correspond to the infusion in conditions of FIGS. 2A and 2B, respectively. Metabolism is zero in FIG. 4A and is characterized by a rate constant corresponding to a half-life of 33.5 hr.
Figure 4B:
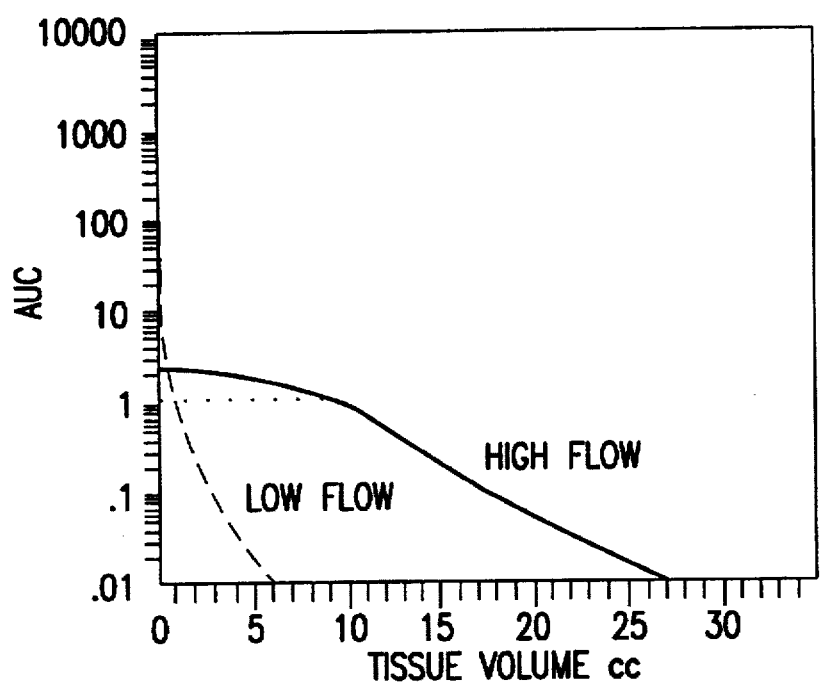

FIGS. 4 and 5 show the pharmacodynamic effect for both metrics as a function of the tissue volume ($4\pi r^3/3$) corresponding to radial position r. FIGS. 4A and 4B contrast the AUC functionalities for high-flow (Eqs. 8 with $\zeta$=0) and low-flow deliveries (Eq. 9) for the same macromolecular parameters and infusion conditions as described in FIGS. 2 and 3. The AUC is much larger in the low-flow situation at short distances from the catheter tip because of the high infusate concentration employed. However, this concentration drops off quickly in a pure diffusional process and, at large distances, the AUC associated with bulk flow infusion exceeds that of the lower flow delivery. The increased treatment volume provided by bulk flow infusion exceeds that of the lower flow delivery. The increased treatment volume provided by bulk flow is indicated by the dotted line in FIG. 4A or 4B for an arbitrary AUC level of unity. The volume increase is 13.2 cm³ (increased penetration of 0.36 cm) when metabolism is absent, and 8.2 cm³ (increased radial penetration of 0.73 cm) when macromolecule is degraded with a characteristic time of 33.5 hr. These correspond, respectively, to nearly a doubling and decade increase over the treatment volume expected for low-flow infusion. The increased treatment volume may be interpreted as the AUC-pharmacodynamic advantage that high-flow microinfusion achieves over low-flow delivery following a 12 hr infusion. Furthermore, this volume increase is not strongly dependent on choice of AUC down to at least 0.1 since the AUC-volume lines are roughly parallel beyond 10.3 cm³.

Figure 5A:
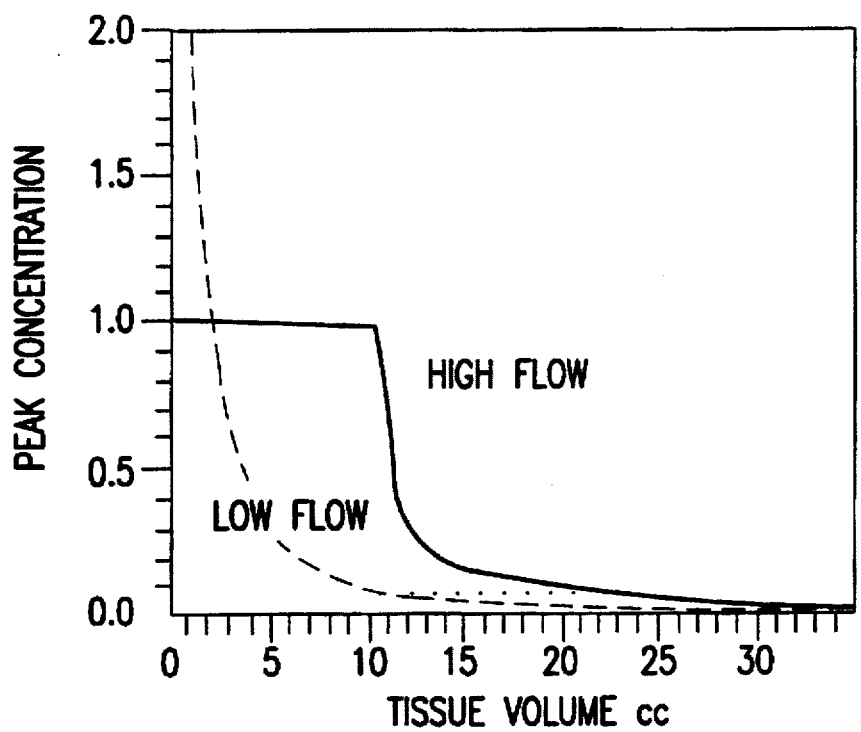
FIGS. 5A and 5B are threshold concentration metric of pharmacodynamic effects as a function of tissue volume corresponding to a radial position r. High-flow and low-flow lines correspond to the infusion condition of FIGS. 2A and 2B, respectively. Metabolism is zero in FIG. 5A and is characterized by a rate constant corresponding to a half-life of 33.5 hr.
Figure 5B:
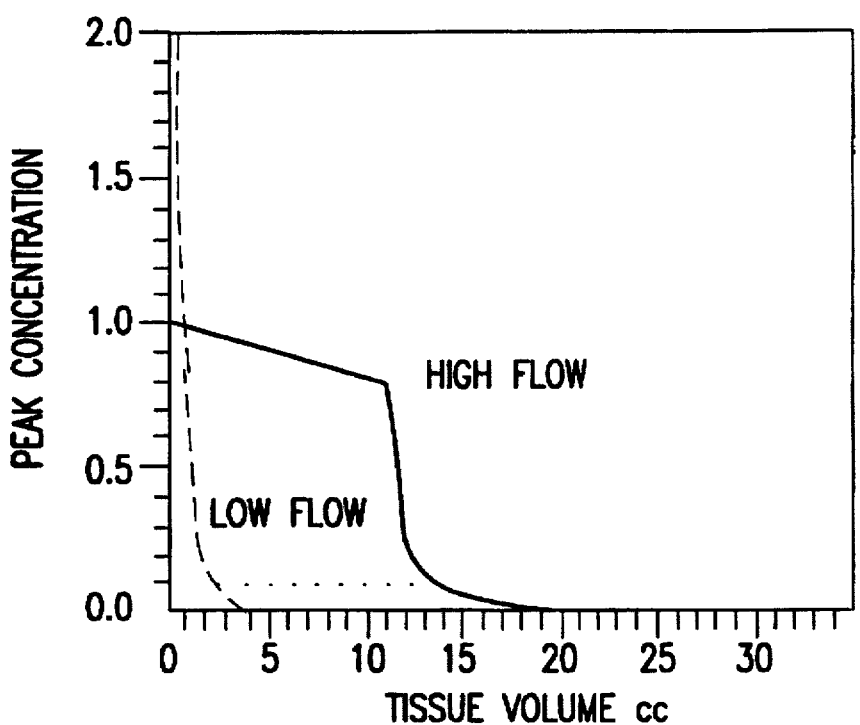

FIG. 5 exhibits the pharmacodynamic results using a threshold metric. To simplify computation, the peak concentration reached at any radial distance r from the catheter tip has been plotted against the corresponding tissue volume. The treatment volume for a given delivery rate of drug was then estimated as the spherical region whose radius was the distance to the 'no effect level', i.e., that distance at which the peak concentration just meets the threshold level but does not exceed it. Outside of this volume, no effect occurs; inside it, significant time is spent above the threshold, the length of this time being the measure of pharmacodynamic magnitude. FIGS. 5A and 5B show these peak concentrations calculated for zero (5A) and 33.5 hr turnover rate ($k_{irr}$=1.15×10⁻⁶ sec⁻¹) (5B) for both high and low delivery rates (other macromolecular parameters and infusion conditions as described in FIGS. 2 and 3). In the case of high-flow microinfusion, peak concentrations at distances within the final infusion volume (r<1.35 cm in FIG. 2, $4\pi r^3/3$<10.3 cm³ in FIGS. 4 and 5) are those that are established when the front first reaches these locations. At distances beyond 1.35 cm, and for the entire radial range of the low-flow delivery case, these peak concentrations occur when diffusional delivery to a point is exceeded by metabolic and microvascular losses. In FIGS. 5A and 5B, the difference between treatment volumes defined by 'no effect' distances is shown as a fine horizontal dashed line for each of the two metabolic rates considered; the threshold concentration was arbitrarily taken as 10% of the high-flow infusate concentration. The relative and absolute volume increases with high-flow microinfusion are similar to those computed for the AUC metric. As above, increased treatment volumes may be interpreted as the threshold-pharmacodynamic advantage that high-flow microinfusion achieves over slow-flow delivery following a 12 hr infusion.

The most significant result of the present invention is the finding that high-flow microinfusion (volumetric inflow rates of 0.5 to 15.0 μl/min) offers the potential of dosing much larger volumes of brain tissue than is possible with low-flow delivery methods. It has been shown that a typical nonbinding 180 kDa macromolecule can be delivered to a 0.36 to 0.73 cm deeper radius, depending on degradation rate, with a 12 hr 3 μl/min microinfusion than with a 0.05 μl/min infusion delivering the same total mass. Corresponding treatment volumes are two to ten-fold larger than is achieved with low-flow infusion, and total treatment volumes are in excess of 10 to 20 cm³. Similar differences would also be expected if high-flow microinfusion were contrasted with a polymer dissolution method in which the same mass were released in 12 hr, since the dissolution method, like the low-flow infusion example, is associated with purely diffusive flux into the surrounding tissue.

A 12 hour infusion period was chosen for comparisons because it may be conveniently accessed clinically, and because it also provides total penetration depths of about 1.5 cm radius, a distance required to perfuse many normal human brain structures as well as the tumors that may arise there. If longer infusion times are considered (e.g., several days) for molecules that undergo little or no degradation, then the theoretical calculations predict a far greater penetration advantage of high-flow over low-flow microinfusion. For example, a 10-day high-flow microinfusion into perfectly homogeneous tissue with a characteristic molecular degradation time of 1 week ($\phi$=0.4, other parameters as in Table 1), is calculated to have a radial penetration advantage over low-flow of more than a centimeter radius and a total penetration of about 3 cm radius.

It is important to observe that the pharmacodynamic advantage of high-flow over lower flow delivery is less than one might expect if only the difference in tissue penetration that exists immediately at the end of infusion were taken as an indicator of eventual effect. For example, comparison of FIGS. 2A and 3A shows that a threshold level of 0.1 $c_o$ is reached at about 1.40 cm in the case of high-flow infusion, but only 0.35 cm in the case of slow-flow delivery, suggesting a penetration advantage of about 1.05 cm. However, the full pharmacodynamic calculation leads to a value of only 0.36 cm, underscoring the great importance of the molecular redistribution that occurs during the post-infusion period. Although the diffusional transport which characterized the post-infusion phase is slow, there is also a very long time available for such diffusion to take place because of the low rates of macromolecular clearance typically encountered in the brain.

Another characteristic of high-flow microinfusion is that the rapid bulk flow tends to keep interstitial concentrations relatively flat over the infusion volume, even through much of the post-infusion period. The transport process itself does not require the presence of concentration gradients, as in the case of diffusion-only delivery methods, and the small residence time in each shell through which the macromolecules pass also diminishes gradients arising from clearance mechanisms. If one is infusing an agent that has a narrow therapeutic window, i.e., a narrow concentration range between unwanted toxicity to surrounding normal tissue and desired effect on target tissue, this flat profile helps assure that the large infused tissue volume does not become exposed to toxic levels. For example, both the AUC and threshold metrics in FIGS. 4 and 5 show that far greater drug effects are likely near the catheter tip for low-flow than for high-flow microinfusion.

Figure 6:
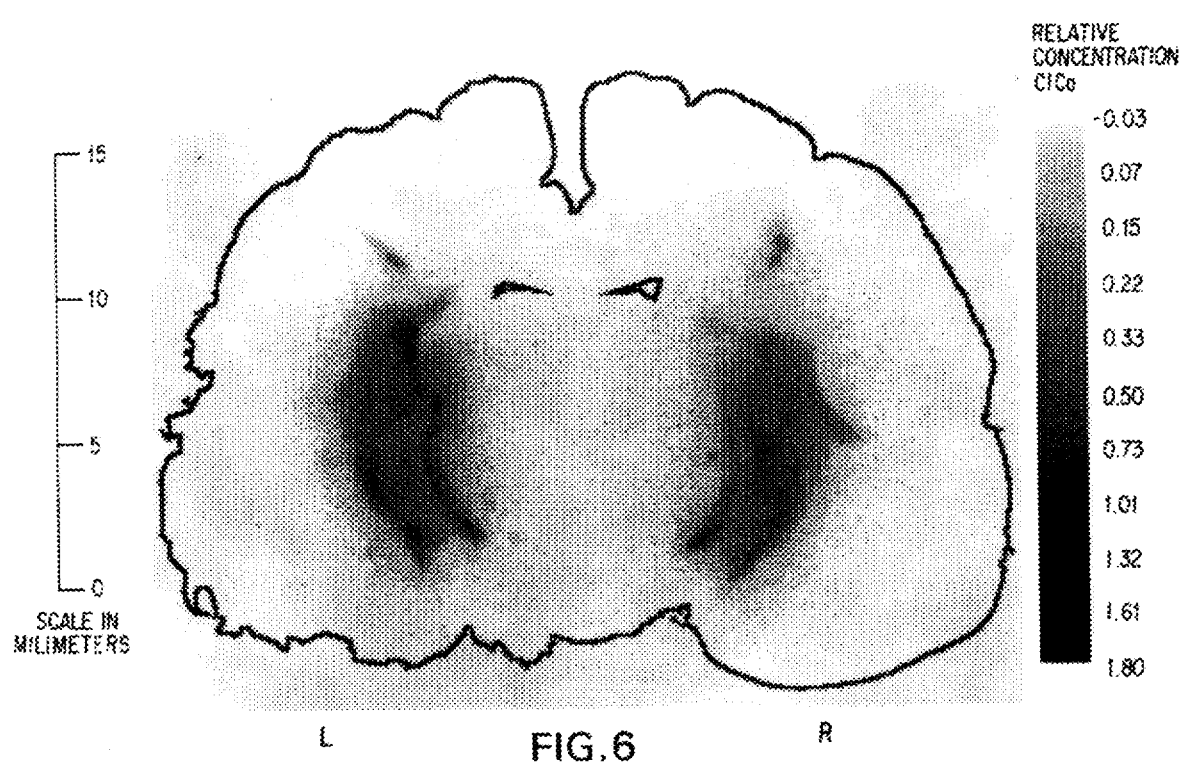
FIG. 6 is an autoradiogram of In$^{111}$-Transferrin in a coronal section of a cat brain.

Theoretical prediction may be compared to preliminary experimental data. FIG. 6 presents the autoradiographic distribution of $In^{111}$-transferrin in a coronal section of cat brain containing the catheter tip location following infusion of a total infusate volume of 75 μl at a mean flow rate of 1.15 μl/min via a catheter placed in the corona radiata. Because of the inhomogeneity and anisotropy of white matter tracts, such an image can not be used to verify details of concentration profiles computed for homogeneous media. However, it is useful in substantiating the predicted order-of-magnitude of penetration with time. Since transferrin is insignificantly bound at the concentrations infused and is confined solely to the extracellular space, the average tissue concentration relative to infusate concentration should be near the extracellular fraction $\phi$. FIG. 6 exhibits concentrations of this magnitude ($\geq 0.2$) over a left-to-right width of about 0.44 cm near the catheter tip location and a distance along the top-to-bottom tract curvature in this section of at least 0.92 cm. Ignoring the possibility of further spread along tracts that turn toward the posterior near the top of this section and toward the brain stem near the bottom, and noting that the left-to-right spread has only begun to cross the white-gray matter interface at this infusion volume, a minimum geometric mean for radial spread of 0.32 cm can be estimated. For comparison, the radial spread predicted by the theory of a homogeneous medium was 0.45 to 0.35 cm depending on the choice of $\phi$ between 0.2 and 0.4.

Potential difficulties of high-flow microinfusion include the possibility of leak-back along the catheter shaft, particularly when infusing into tissue with high resistance at inflow rates exceeding 5 μl/min. However, tests have shown that the likelihood of this event may be nearly eliminated in white matter by using lower flow rates (e.g., at or less than 1 μl/min with a 27 ga. needle) or a schedule of sequentially increased flows (e.g., 0.5 μl/min to 4 μl/min stepping every 15 to 30 min). Another difficulty is prediction of detailed behavior in anisotropic media such as the white matter. Distribution in the gray matter is spherical as found with phytohemagglutinin distribution in gray matter (Lieberman et al, personal communication). However, as shown in FIG. 6, materials do not distribute spherically in white matter due to the greater tendency of molecules to flow in the direction parallel to the fiber tracts rather than perpendicular to them.

The following example is presented to illustrate features and characteristics of the present invention which is not to be considered as limited thereto.

Example 1

Figure 7:
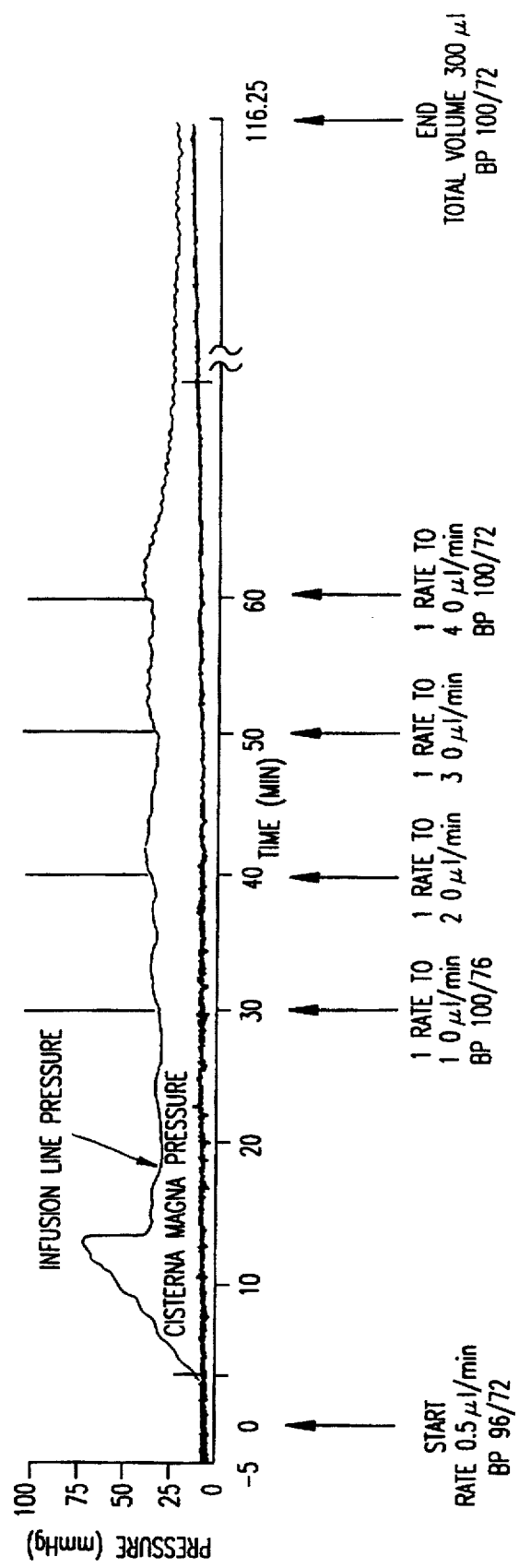
FIG. 7 is a plot of infusion pressure over time for a high-flow microinfusion procedure.

In this example artificial CSF containing $indium^{111}$-transferrin ($In^{111}$-Tf; MW=80,000) and $C^{14}$-sucrose (MW=359) was infused for 2 to 4 hours into the corona radiata bilaterally in 12 anesthetized cats (24 hemispheres) while cicterna magna, arterial, and infusion pressure were monitored. FIG. 7 shows the physical parameters over time during a typical high-flow microinfusion. During each infusion there was an initial interval (mean infusion time, 18 minutes) of increasing pressure in the infusion line (during this phase of the infusion the infusion rate was 0.5 μl per minute) to reach a peak pressure of 57±24 mmHg (mean±SD, n=12). This was followed by a rapid decrease in infusion pressure to a stable pressure of 26±9 mmHg (n=12). Mean intracranial pressure remained at 8±2.5 mmHg (n=8) during the infusion procedure. The convection pressure gradient was estimated by the difference between infusion pressure and intracranial pressure after the plateau phase had been reached. The convection pressure at plateau was 18±3 mmHg (n=8) during infusion at 0.5 μl per minute during the first 20 μl infused and then gradually decreased to 10±4 mmHg (n=8) at 4.0 μl per minute as the infused volume reached 300 μl. The effects of infusion volume (75,300 or 600 μl per hemisphere), molecular weight, and redistribution over time (0, 2 and 24 hours) on the volume of distribution ($V_d$) of the infused compounds were studied.

The stereotactic coordinates used for the infusion cannulae were Anterior-Posterior (AP) +12.6, Vertical +5.0 and Horizontal +8.5 mm. Infusion line pressure, cicterna magna pressure, blood pressure and electrocardiogram were recorded.

Infusions were performed with a syringe pump (model 22 Harvard). 5 cm stainless steel 23 g blunt infusion cannulas were connected to 3 ml syringes with 60 cm of tubing.

To prepare the infusate a solution of endotoxin-free iron-poor human transferrin was prepared in 0.25M trischloride and 10 m/M $NaHCO_3$, pH 8.0. 400 μl of this solution was added to 200 μl of 0.04M HCL solution containing approximately 2 mCi of $indium^{111}$ chloride and incubated at 37° C. for 1 hour. The solution was then layered on a column (PD-10, Pharmacia, Uppsala, Sweden) and eluted with phosphate-buffered saline, pH 7.4. Radioactivity in eluted fractions was detected with a gamma counter. Recovery of indium was greater than 95% in pooled fractions containing indium-transferrin. The solution prepared for infusion contained $In^{111}$-Tf (0.3 mCi/ml), $C^{14}$-sucrose (2 μCi/ml) and dextran blue (MW $2 \times 10^6$, 2.8 mg/ml) in PBS, pH 7.4, osmolarity 314.

Animals were euthanized at 0, 12, and 24 hours after completing an infusion, the brain was removed and cut into 8 mm thick coronal sections, which were placed on coverslips and frozen on dry ice. Samples of CSF, blood, liver, kidney and muscle were obtained and weighed. 20 μm coronal brain sections were then cut on a cryostat; six sections were obtained at 1 mm intervals through the brain (4 for autoradiography, 2 for histology). Double-label quantitative autoradiography (QAR) was performed as described by Blasberg et al (Brain Edema J. Cervos-Navarro, R. Ferszt, Eds. (Raven Press, N.Y. 1980), vol. 28, pp. 255–270). QAR $In^{111}$ standards were prepared from homogenized brain at concentrations of 0.01 to 0.8 relative to the infusate $In^{111}$ concentration. $In^{111}$-Tf present in the brain sections was allowed to decay for more than 12 weeks (30 half lives) before exposing the section for $C^{14}$ determination. Sections for histology were stained with luxol fast blue-periodic acid Schiff stain and Hematoxylin and eosin.

Image analysis was performed on a Macintosh IIfx computer using the program "Image" (NIH public domain software available on Internet). A high-resolution video camera was used in combination with a precision illuminator to digitize the autoradiograms. For each coronal section containing isotope, the area of the distribution containing a minimum concentration of isotope (relative to infusate concentration) was determined for minimum threshold concentration ranging from 0.01 to 0.8. Volumes of distribution were determined by summing areas of distribution over the volume of brain containing isotope.

Systemic concentrations of $In^{111}$-Tf were determined by gamma counting of weighed samples of blood, liver, kidney and muscle from each animal after sacrifice. $C^{14}$-sucrose concentrations in these tissues was determined by scintillation counting of homogenized samples after letting the $In^{111}$ decay for 2 months (>20 half lives).

Figure 8:
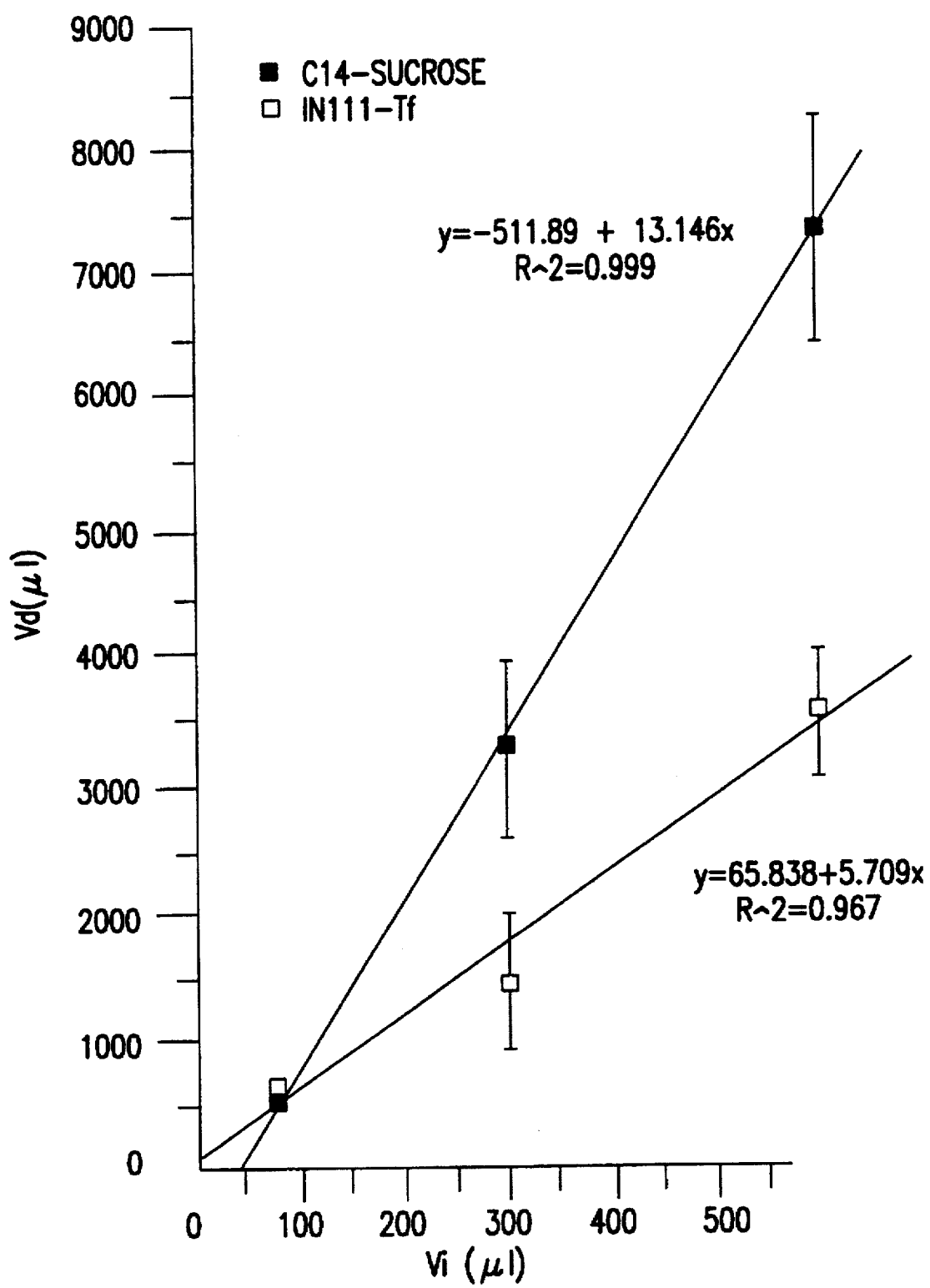
FIG. 8 is a plot of the volume of distribution ($V_d$) versus volume of infusion ($V_i$). The $V_d$ containing $\geq 1\%$ of infusate concentration is graphed against the infusion volume ($V_i$) got In$^{111}$-Transferrin (MW 80,000) and C$^{14}$-sucrose (MW 359) in animals sacrificed immediately after infusion. Infusion volumes of 75 μl, 300 μl, and 600 μl per hemisphere were studied. The slope of $V_d/V_i$ was 6:1 for In$^{111}$-Transferrin and 13:1 for C$^{14}$-sucrose, as determined by regression analysis (p<0.01).

The $V_d$, the anatomic distribution, and concentration profiles in the brain were determined by quantitative autoradiography and computerized image analysis. Fractional concentrelatis of $In^{111}$-Tf and $C^{14}$-sucrose relative to the infusate concentration were used to define volumes of distribution ($V_d$) of infusate in the brain. Thus, each $V_d$ contained a concentration of Tf or sucrose greater than or equal to a certain fraction concentration of infusate. The lowest measured concentration of Tf and sucrose, relative to the concentration in the infusate, was 1%. In FIG. 8, the $V_d$ containing $\geq 1\%$ of infusate concentration is graphed against the infusion volume (Vi) for $In^{111}$-Tf and $C^{14}$-sucrose in animals sacrificed immediately after infusion.

The $V_d$ containing $\geq 1\%$ of the infusate concentration increased linearly with the infusate volume ($V_i$) for $In^{111}$-Tf and $C^{14}$-sucrose. $V_d/V_i$ remained constant at 6:1 for $In^{111}$-Tf and at 14:1 for $C^{14}$-sucrose, as determined by regression analysis (p<0.01). Immediately after completion of infusion of 600 µl, approximately 50 percent of the cat hemisphere had received $\geq 1\%$ of the concentration of $In^{111}$-Tf in the infusate. Since diffusion of Tf over 3 hours of infusion was negligible, this distribution was attributed to convection.

Figure 9A:
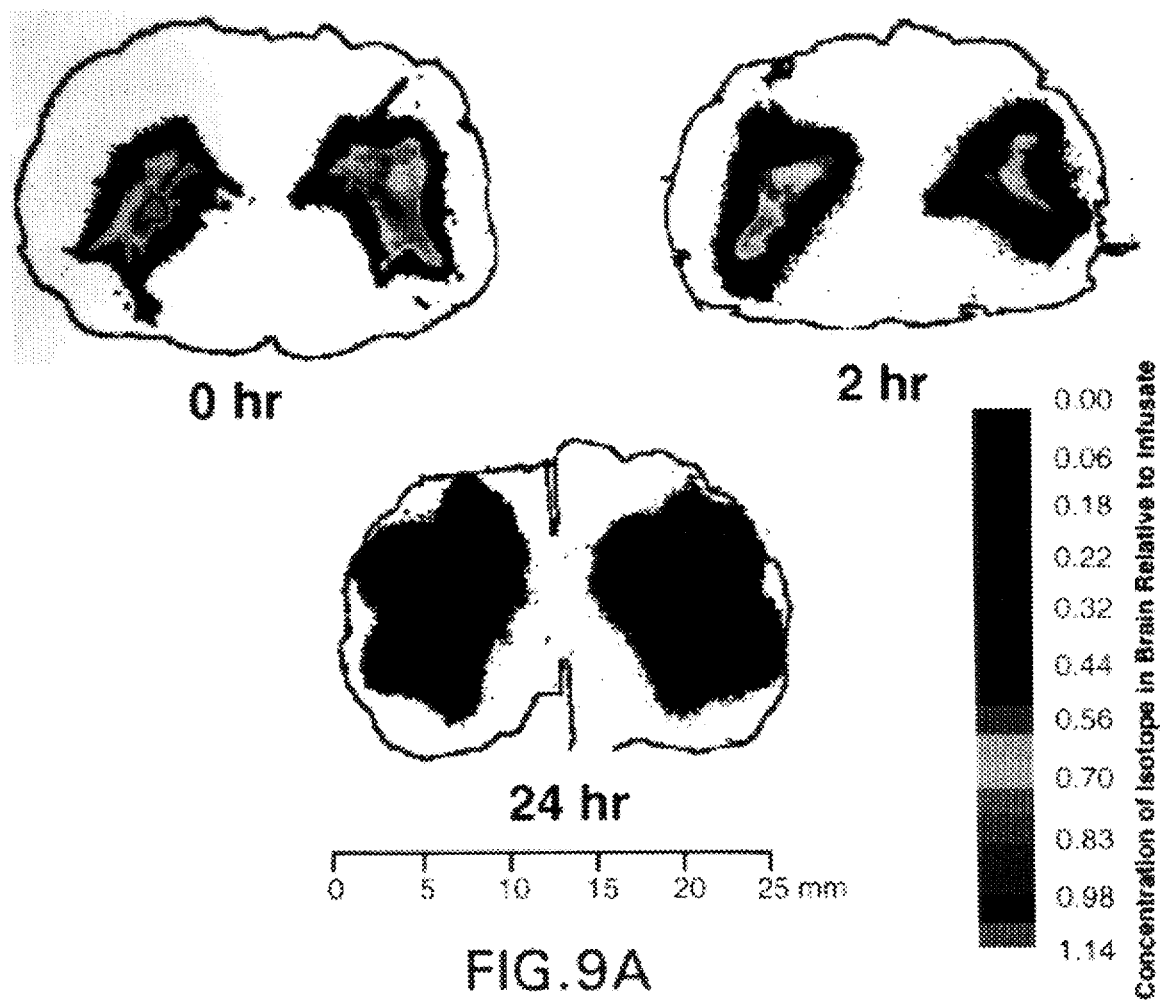
FIG. 9A and 9B are autoradiograms of In$^{111}$-Transferrin and $^{14}$C-sucrose infused into a cat brain using the high-flow microinfusion delivery technique.
Figure 9B:
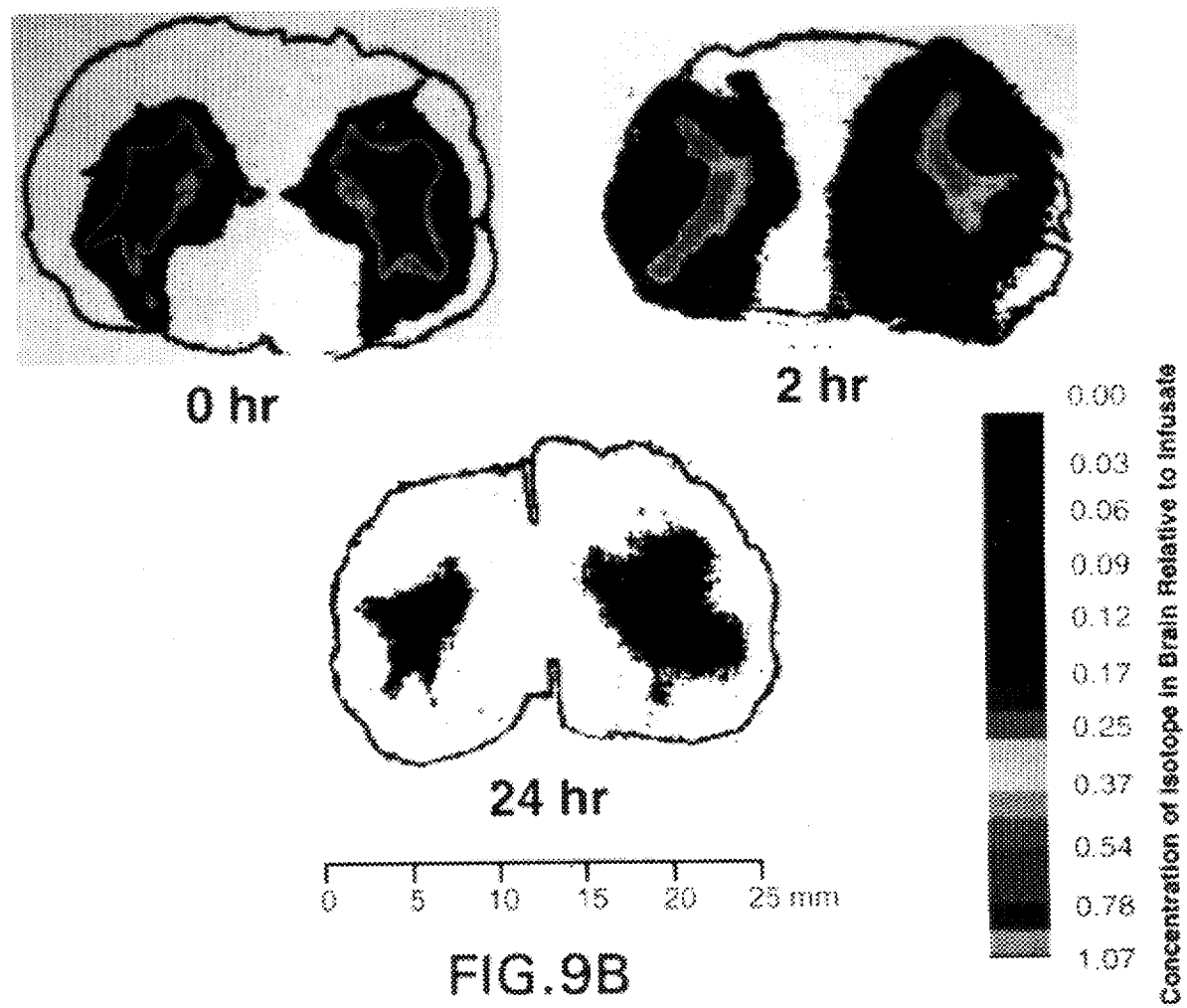
Figure 14:
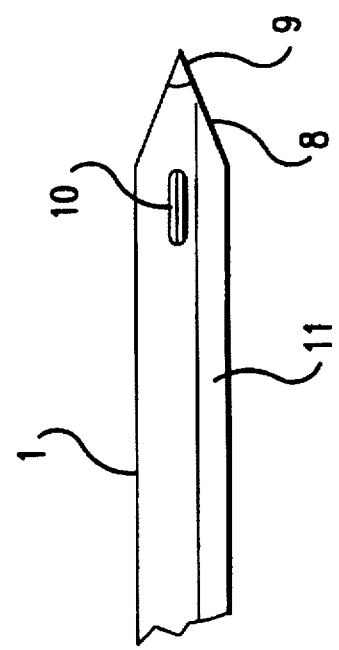
Figure 15:
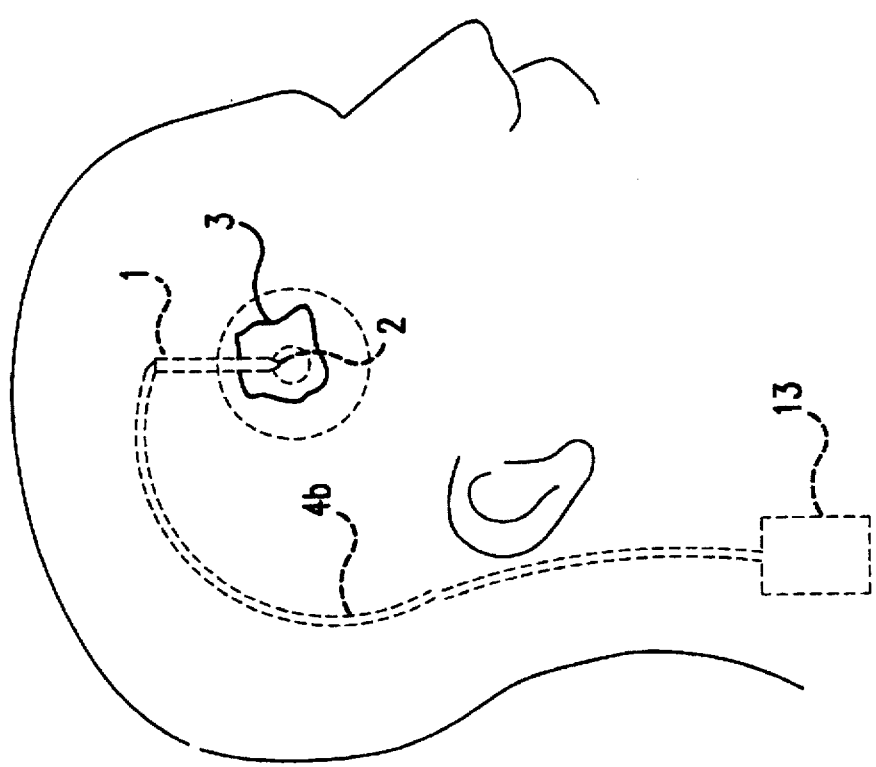

FIGS. 9A and 9B are autoradiograms of $In^{111}$-transferrin (FIG. 9A) and $C^{14}$-sucrose (FIG. 9B) obtained after 300 µl of artificial CSF containing indium$^{111}$-transferring ($In^{111}$-Tf; MW 80,000) and $C^{14}$-sucrose (MW 359) was infused for 2 to 4 hours into the corona radiata bilaterally. 9A) $In^{111}$-Tf profiles in coronal sections within 1 mm of the infusion site are shown for representative animals from each time point. 9B) $C^{14}$-sucrose concentration profile at 0, 2 and 24 hours after infusion. $C^{14}$-sucrose profiles in coronal sections within 1 mm of the infusion site are shown for animals from each time point.

After the infusion was complete, the $V_d$ containing $\geq 1\%$ of the infusate concentration increased for Tf over 24 hours and increased for sucrose for at least 2 hours as shown in FIGS. 9A and 9B. As can be seen from FIGS. 9A and 9B, there was a significant decrease (p<0.01) in the $V_d$ which contained $\geq 60\%$ of the infusate concentration for both Tf and sucrose from 0 to 24 hours after infusion. Thus, the concentration profiles of sucrose and Tf were increasingly homogeneous over time after the infusion was completed.

After drug placement in the brain interstitium, limited distribution of drugs by diffusion in the brain, or in brain tumors, constrains the treatment volume. For example, slow continuous infusion of cis-diamminedichloroplatinum(II) into brain affects about one cubic centimeter and is associated with a one hundred-fold decrement in concentration over less than five millimeters radial distance. For high molecular weight compounds, low diffusivity in brain, or in tumor, relative to tissue clearance limits distribution. For low molecular weight compounds capillary loss and metabolism often underlie the restricted distribution. The short distribution distances and the steep concentration gradients associated with diffusion limit the utility of purely diffusive drug delivery for regional therapy of CNS disorders. The present invention demonstrates that it should be feasible to exploit fluid convection to enhance drug transport through regions of brain or tumor.

Infusion rates are critical for successful induction of convection in brain. Rates of infusion greater than a few microliters per minute produce leakage of infusate out the cannula tract and loss of infusion pressure. Since the CNS can remove fluid from the interstitial space in edematous white mater at about 0.3–0.5 µl/min/cm$^3$, equivalent to about 2.5 µl/min per hemisphere in the cat, much slower rates of infusion limit the attainable volume of distribution at a specific drug concentration. By incrementally increasing the infusion rates from 0.5 µl/min to 4.0 µl/min., the present invention distributes transferrin to an extent considerably exceeding that which would occur by diffusion alone. Two-hour infusions spread transferrin approximately 1.5 cm in a rostral-caudal direction immediately after completing the infusion. Furthermore, the $V_d$ containing $\geq 1\%$ of the infusate concentration increased linearly with $V_i$ for $^{111}$In-Tf and $^{14}$C-sucrose with the infusion volumes tested, suggesting that a maximum $V_d$ had not been reached. The maximum $V_d$ that can be achieved from a single drug source by this delivery method has not yet been defined.

For reference, one may compare the 1.5 cm penetration distance that occurred during high-flow microinfusion to the penetration depth expected for planar diffusion of the infusate solution into brain tissue. This depth, x, calculated to an average tissue concentration of 1% of the infusate concentration, is given by $0.01/\Phi = \mathrm{erfc}(x/\sqrt{4Dt})\exp(-Kt)$ where $\Phi$ is the extracellular fraction, D is the tortuosity-corrected diffusion coefficient in the extracellular space, and K is the capillary permeation loss rate per unit volume of extracellular space. Assuming a D of $8\times10^{-8}$ cm$^2$/sec for transferrin in brain, a $\Phi$ of 0.2, and negligible K, then this penetration depth is 0.07 cm at 2 hours. For sucrose, taking $D=3.1\times10^{-6}$ cm$^2$/sec and $K=3.5\times10^{-5}$ sec$^{-1}$, this penetration depth increases to 0.39 cm. For both chemical species, but especially for the macromolecule, diffusion thus exposes a significantly smaller volume of distribution than does high-flow microinfusion.

Alternatively, one may compare the 1.5 cm bulk flow penetration diameter with that expected from a much slower point infusion into homogeneous media in which it is assumed that the same amount of mass is infused over 2 hours, but that all tissue transport is diffusional, due to the choice of a very low volumetric flow. This diameter can be obtained from the time-dependent expression for the tissue-averaged radial concentration profile c(r, t) about a slow flow (diffusional) source.

$$c(r,t) = \frac{Q}{8\pi r D} [\exp(r\sqrt{K/D})\mathrm{erfc}(r/\sqrt{4Dt} + \sqrt{Kt}) +$$

$$\exp(-r\sqrt{K/D})\mathrm{erfc}(r/\sqrt{4Dt} - \sqrt{Kt})]$$

where K and D are defined as above, $t+2$ H, and Q $c_0 q_v$ is the mass infused per unit tim, equal here by assumption to the product of the high-flow infusate concentration ($c_o$) by its volumetric flow rate ($q_v=3$ µl/min). The diffusional penetration diameter sought is the value of 2r when c(r,t=2 h) is 1% of $c_o$. This distance is computed to be only 0.28 cm and is clearly a much smaller penetration distance than obtained experimentally when the infusion is such that bulk flow is dominant. This represents only about 1/100th the volume accessed by bulk flow. A similar calculation for sucrose at low flow shows less difference, yielding a penetration distance that is only somewhat less than that achieved at high flow (1.1 vs 1.5 cm) and a volume ratio of 0.39.

The infused macromolecule, transferrin, is capable of binding to transferrin receptors and being internalized by cells bearing those receptors. When active, such processes are capable of affecting both the magnitude and timing of spread. However, these complications were avoided in the present experiments by infusion of transferrin solutions at concentrations that were nearly 5 logs in excess of reported tissue-averaged brain transferrin-receptor densities of 0.04 nM. Maximal rates of endocytosis have been measured in teratocarcinoma stem cells at one full receptor complement every 6 min. Applied to the brain receptor density, this translates into a maximal uptake rate of 0.007 nM/min. A 4 h infusion of our transferrin solution would therefore lead to a concentration reduction of only −0.015% near the leading edge of the infusion profile.

The magnitude and spread of the edema generated by high-flow microinfusion is dependent upon the infusion rate and total volume infused. At a maximum flow rate of 4 μl/min, the relative concentration nears unity along several millimeters of the white fiber tracts (FIG. 3) and is significantly more than expected for the displacement of the extracellular fluid of normal white matter. While relative concentrations near unity are expected for a very small volume about the catheter tip due to displacement of brain mass and its replacement by pure infusate, other effects must be responsible for the occurrence of such values over the scale observed. One explanation is the extracellular expansion created by the infusion pressure acting through the highly non-linear relationship between tissue hydraulic conductivity and extracellular volume, as well as the large elasticity of white matter. This is supported by histologic observations in which the white matter bundles in the infused areas were observed to be more separated within a few millimeters of the catheter tip than elsewhere with no evidence of cyst formation. In addition, since edema expansion alone is insufficient to raise relative concentration values to unity, some filtration of water is probably occurring in the vicinity of the catheter tip. It is conceivable that the mechanical expansion of the white matter (greater than that expected for gray matter) stretches the endothelial junctions and increases the capillary permeability to water, producing a filtration concentration. Because such water removal would tend to reduce tissue pressure with distance from the catheter, the greatest hydraulic pressure and filtration should exist near the tip. Hence, concentrated solutions created near the tip could then flow to more distant region with little further water loss, thus explaining the concentration patterns seen in FIG. 3.

All of the interstitial brain infusions performed during the course of the present invention were well tolerated and were associated with no hemodynamic instability during the infusions. The two animals that were allowed to recover from anesthesia demonstrated transient lethargy and weakness that resolved by 24 hours. The chronic effects of interstitial brain infusion, which are known from previous studies of infusion edema, are mild and are probably functionally insignificant. In an infusion edema model in cats Nakamura et al, *In Brain Edema* (1984); Y. Inaba, I. Klatzo and M. Spatz, Eds., Springer-Verlag: Berlin, pp. 490–493, demonstrated that white matter brain edema of about 80% g H$_2$O/g tissue beneath the sensorimotor area caused no neurologic dysfunction. In structural studies of infusion edema in cats by Marmarou et al, *In Brain Edema; J. Cervos-Navarro and R. Ferszt. Ed.*; Raven Press: New York Vol. 28; pp 345–358, the myelinated axons remained spatially related via oligodendroglial processes, despite the expansion of the extracellular space, and there was orderly reconstitution of the tissue as the edema resolved, leaving only a mild fibrillary astrocytosis. This is consistent with the present findings in cats which received infusions similar to those reported here with mock CSF and which were followed for 30 days after infusion. They remained neurologically normal, MRI scans showed resolution of edema by one week, and histology at 30 days revealed mild gliosis in the area of infusion edema (unpublished data).

In a variety of experimental modes, cerebral edema does not cause neurologic dysfunction as long as intracranial pressure is not appreciably elevated. In a study by Rapoport and Thompson, *Science* 180: 971, vasogenic edema caused by hyperosmotic blood-brain barrier disruption in nonhuman primates resulted in no neurologic dysfunction or behavior change. In a study of experimental brain tumors by Hossmann et al, *Adv. Neurol* 28: pp. 323, vasogenic peritumoral edema caused no change in cerebral blood flow, autoregulation of cerebral flood flow, or the electroencephalogram if intracranial pressure remained normal. Furthermore, neurologic deficits associated with cerebral edema in patients with brain tumors are reversible following reduction of peritumoral edema with medical therapy, suggesting that even when edema is severe enough to cause neurologic dysfunction, deficits related to edema are reversible. Thus, evidence from experimental clinical studies indicate that cerebral edema per se does not alter brain function as long as there are no associated herniations of cerebral tissue, significant elevation of intracranial pressure, or reduction of cerebral blood flow below the normal range.

Convection can be used to supplement diffusion for distribution of certain compounds to treat much larger volumes of brain than can be achieved by diffusion alone, and with a very great pharmacokinetic advantage over systemic administration. After systemic administration, macromolecules rarely reach concentrations of CNS extracellular fluid of 1% of plasma concentration. After interstitial infusion brain concentrations of Tf and sucrose were more than a hundred-fold high than systemic concentrations. The technique described here has the potential of overcoming some of the drug delivery problems imposed by limited drug diffusion through the brain interstitium when attempting to circumvent the BBB by delivering drugs directly into brain parenchyma. Moreover, it is to be understood that the technique of the present invention is not strictly limited to use in conjunction with brain tissue or brain tumors. In this regard, the technique disclosed herein is applicable to any type of solid tissue or solid tumor. This technique for drug delivery may also enhance drug distribution in tumors in the CNS and elsewhere.

FIG. 10 shows a convection-enhanced drug delivery system developed by the inventors during the course of the present invention. The system includes an infusion catheter 1, which has a diffusion tip 2 that is inserted in a tissue situs where a drug or agent is to be infused. For example, FIG. 10 illustrates the tip 2 of the infusion catheter 1 as being in a central portion of a tumor 3.

A connecting tubing 4 connects the infusion catheter 1 to a syringe 5. For convenience, the connecting tubing can include two or more sections 4a and 4b which are connected at an intermediate position by means of a conventional connector or coupler 6. The syringe 5 is attached to a programmable syringe pump 7 of conventional design.

Alternatively, the connecting tubing 4 could connect to the reservoir of an implantable pump of conventional design.

In operation, the infusion catheter 1 is positioned so that the infusion tip 2 thereof is in a desired situs. The connecting tube 4 is connected between the infusion catheter 1 and a syringe 5 which is mounted on the programmable syringe pump 7. The programmable syringe pump 7 is operated as desired to provide constant, ramped, or a stepped increase of pressure for a desired period of time as discussed above. This procedure could also be performed with an implanted pump.

FIGS. 11 and 12 depict an infusion catheter designed for providing convection-enhanced drug delivery according to the present invention. FIG. 11 is a side view of the infusion catheter 1. The infusion catheter is cylindrical and includes a tapered end portion 8 having a tip 9 which includes or is impregnated with a detectable marker such as barium which allows for monitoring of the positioning of the tip 9 during an infusion or by CT scan or conventional x-rays. A plurality of parallel slit openings 10 are provided adjacent the tapered portion 8 of the infusion catheter 1. These parallel slit openings 10 are symmetrically spaced around the circumference of the catheter. In the preferred embodiment, depicted in FIG. 11, three slit openings 10 are provided and spaced 120° apart along the circumference of the infusion catheter 1.

The slit openings 10 have a particular design which overcomes a problem encountered during the development of the present invention. In this regard, it is necessary to implant the catheter 1 or position the tip 9 of the catheter 1 with the catheter 1 fully loaded with an agent or biocompatible solution to be delivered so as to avoid introducing any air into the tissue situs in cases wherein the introduction of air into a tissue situs is to be avoided. At the same time, care should be taken so as not to interject an agent into an undesired situs while implanting the catheter 1 or positioning the tip 9 of the catheter 1. For example, the release of a toxic agent from the catheter 1 has to be very carefully controlled.

In order to ensure that an agent loaded into the catheter before positioning thereof does not leak out uncontrollably, it was determined that narrow slit openings or "slit valves" were necessary. These slit openings 10 function as valves because the slits remain closed until fluid pressure within the catheter 1 forces the slits open. In this manner, the slit openings or "slit valves" effectively prevent the loaded agent from leaking out of the catheter 1 until a pressure gradient is applied according to the present invention.

In addition to preventing the loaded agent from leaking out of the catheter during implanting the catheter or positioning the tip of the catheter, it was discovered that the slit openings or "slit valves" according to the present invention prevented leakage of the agent from the catheter also prevented material from the tissue situs from entering the catheter through the slit openings. It was further found that alignment of the slit openings 10 along the axis of the catheter 1 and positioning the slit openings behind the tapered portion 8 of the catheter tip 9 as depicted in FIG. 11 helped prevent the slit openings 10 from collecting material from the tissue situs as the catheter is inserted into the tissue situs and becoming clogged or blocked.

The catheter 1 includes a inner channel 11 which is best illustrated in FIG. 12. FIG. 12 is a cross-sectional view of the infusion catheter 1 and illustrates the positioning of the slit openings 10 in the catheter wall and the channel 11. The channel 11 is provided to receive a wire stylet 12 which is illustrated in FIG. 13.

The infusion catheter can be made of any suitable biocapable material, e.g. silicone, which is sufficiently resilient so that the slit openings open when fluid pressure is exerted within the catheter. The dimensions of the catheter can be varied depending upon the particular situs to which drug delivery is desired. In an exemplary embodiment, designed for drug infusion in a human brain, a catheter having a length of approximately 30 cm, an outside diameter of approximately 2.1 mm and an inside diameter of 1.2 mm was designed. In this embodiment, the stylet chamber had a cross-sectional area which was comparable to a diameter of approximately 0.1 mm.

The infusion catheter can be positioned using known stereotactic procedures and by monitoring the detectable tip of the infusion catheter. It is also possible to provide the catheter with conventional devices such as a trocar, a lunar lock connector, a rear-end plug for the catheter, a fixation collar to secure the catheter and a plastic collar with a fixation or set screw to provide a depth stop for stereotactic catheter placement.

The infusion enhanced drug delivery system of FIG. 10, which includes the infusion catheter illustrated in FIGS. 11 and 12 is used by first programming a pump to infuse a desired amount of drug solution. According to one example, the syringe pump is programmed to deliver 0.5 µl/min. for 30 minutes, then 1.0 µl/min. for 10 minutes, then at 2.0 µl/min. for 10 minutes, then 3.0 µl/min for 10 minutes and thereafter 4.0 µl/min. until a target volume of drug solution is reached. After the syringe pump is programmed and the catheter is loaded with a desired agent, the infusion catheter 1 is positioned using stereotactic placement procedures and by detecting the position of the detectable tip 9. Once positioned, the distal end of the catheter is connected to a fluid loaded syringe 5 using the connecting tubing 4 while avoiding air bubbles. According to an alternative embodiment, it is within the scope of the present invention to include an implanted pump with a reservoir having a predetermined volume of a drug solution which is connected to tubing 4.

Once the syringe 5 is connected to an infusion catheter 1, infusion is started using the preprogrammed syringe pump 7. Infusion is stopped once a target volume has been reached. If necessary, an estimate of the volume of distribution of the infused fluid can be obtained by magnetic resonance imaging after one to two hours of infusing. For such a procedure, a high signal on the T2 sequences will identify areas penetrated by infused fluids.

Convection can be used to supplement diffusion for distribution of certain compounds to treat much larger volumes of brain than can be achieved by diffusion alone, and with a tremendous pharmacokinetic advantage over systemic administration. The technique of the present invention has the potential of overcoming some of the drug delivery problems imposed by limited drug diffusion through the brain interstitium.

A major benefit of high-flow microinfusion is control over the delivery process. Due to its relatively rapid rate of delivery (when binding is weak or infused concentrations are well above binding concentrations), it allows homogeneous tissues (e.g., gray matter) of at least 1 to 2 cm radius to be dosed rather uniformly, thus providing control over the undesired toxicity that often arises with methods that generate large concentration gradients over the entire infusion volume. High-flow microinfusion provides deep penetration depths while avoiding either the potentially toxic high infusate concentrations or much longer infusion times require to achieve the same penetration by low-flow delivery. Because microinfusion only involves stereotactic placement of the catheter, this technique also enjoys an advantage over polymer dissolution techniques where placement of the polymer involves more extensive surgery and disturbance of surrounding tissues. Furthermore, because the interstitial velocities generated by high-flow microinfusion can exceed those present endogenously, this technique is less affected than diffusion-dependent techniques by the unpredictable patterns of normal bulk flow in brain tissue.

Finally, high-flow microinfusion has the potential of being broadly applicable. It is potentially applicable in the administration of targeted protein toxins, antibodies for treatment or imaging, proteins in enzyme replacement therapy, growth factors in the treatment of various neurodegenerative disorders, DNA, RNA and viruses in gene therapy. One particular agent for which the present invention has been found to be particularly useful in administrating is transferrin CRM107.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

We claim:

1. A method of administering a fluid pharmacological agent to a solid tissue through direct convective interstitial infusion and over a predetermined time comprising:

inserting a catheter directly into said tissue; and administering said agent under pressure through said catheter into the interstitial space at a flow rate of from about 0.5 µl/min to about 15 µl/min.

2. The method of administering a fluid pharmacological agent according to claim 1, wherein the fluid pressure is increased in one or more steps.

3. The method of administering a fluid pharmacological agent according to claim 1, wherein the fluid pressure is continuously increased over at least part of said predetermined time.

4. The method of administering a fluid pharmacological agent according to claim 1, wherein the fluid pressure is continuously increased over all of said predetermined time.

5. The method of administering a fluid pharmacological agent according to claim 1, wherein said pharmacological agent comprises a macromolecule.

6. The method of administering a fluid pharmacological agent according to claim 1, wherein said pharmacological agent is selected from the group consisting of a protein toxin, an immunotoxin, an antibody, a protein, a growth factor, a virus, a DNA, a RNA, an imaging agent and mixtures thereof.

7. The method of administering a fluid pharmacological agent according to claim 1, wherein said solid tissue is brain tissue.

8. The method of administering a fluid pharmacological agent according to claim 1, wherein said solid tissue is a tumor.

9. The method of administering a fluid pharmacological agent according to claim 1, wherein the fluid pressure is increased by means of a programmable pump.

10. The method of administering a fluid pharmacological agent to a solid tissue according to claim 1, further comprising increasing the pressure of said fluid agent at least once over the predetermined time.

11. A method for treating a solid tumor comprising:

inserting a catheter into said tumor; and, administering a fluid pharmacological agent directly into interstitial spaces of said tumor through said catheter at a flow rate of from about 0.5 µl/min to about 15 µl/min.

12. The method of treating a solid tumor according to claim 11, further comprising increasing the pressure of said fluid agent at least once over a predetermined time of administration.

13. In a method of administering a fluid pharmacological agent to a dense tissue, the improvement comprising administering said agent directly into an interstitial space of said tissue through a catheter at a rate of from about 0.5 µl/min to about 15 µl/min over a predetermined time, wherein the fluid pressure is increased at least once over said predetermined time.

* * * * *